(12) United States Patent
Wipf et al.

(10) Patent No.: US 6,392,055 B1
(45) Date of Patent: May 21, 2002

(54) SYNTHESIS AND BIOLOGICAL EVALUATION OF ANALOGS OF THE ANTIMITOTIC MARINE NATURAL PRODUCT CURACIN A

(75) Inventors: Peter Wipf; Jonathan T. Reeves; Billy W. Day; Raghavan Balachandran, all of Pittsburgh, PA (US)

(73) Assignee: The University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/909,076

(22) Filed: Jul. 19, 2001

Related U.S. Application Data

(60) Provisional application No. 60/219,283, filed on Jul. 19, 2000, and provisional application No. 60/246,186, filed on Nov. 16, 2000.

(51) Int. Cl.[7] .................... C07D 277/22; C07D 263/32
(52) U.S. Cl. .................... 548/203; 548/146; 548/235; 548/239
(58) Field of Search .................... 548/203, 146, 548/235, 239

(56) References Cited

U.S. PATENT DOCUMENTS

| | | | |
|---|---|---|---|
| 5,324,739 A | 6/1994 | Gerwick et al. | |
| 5,795,909 A | 8/1998 | Shashoua et al. | |
| 5,886,025 A | 3/1999 | Pinney | |
| 5,919,815 A | 7/1999 | Bradley et al. | |
| 6,057,348 A | 5/2000 | Gerwick et al. | |

OTHER PUBLICATIONS

Verdier–Pinard, et al, 1998, Mol. Pharmacol., 53(1), 62–76.*

* cited by examiner

*Primary Examiner*—Robert W. Ramsuen
*Assistant Examiner*—Andrea D'Souza Small
(74) *Attorney, Agent, or Firm*—Thorp Reed & Armstrong LLP

(57) ABSTRACT

The present invention provides an efficient synthetic strategy for the preparation of analogs that incorporate important structural elements of the marine natural product curacin A, the compositions and various uses of the compositions. The most active of these compounds at nanomolar concentrations inhibit tubulin polymerization, show growth inhibition activity, inhibited colchicines binding to tubulin and block mitotic progression. The compounds of the present invention represent some of the most potent synthetic curacin A analogs synthesized, with an activity profile rivaling that of the natural product despite the simplified structure, greater water solubility, and increased chemical stability.

7 Claims, 15 Drawing Sheets

CURACIN A (1)

COLCHICINE (2)

Synthesis of Aldehyde Intermediates

Synthesis of Targets

JRoxime1

JRC1

JRoxime2

JRC2

JRoxime3

JRC3

JRC5

JRC4

JRCPOX

JRDCCA

Additional Oxime Analogs:

Additional Oxime Analogs:

Synthesis Of JRoxime1

Representative plots comparing inhibition of GTP/glutamate-induced assembly of tubulin by 40 nM - 1 μM concentration of JRoxime1 and curacin A.

SYNTHESIS AND BIOLOGICAL EVALUATION OF ANALOGS OF THE ANTIMITOTIC MARINE NATURAL PRODUCT CURACIN A

This application claims the benefit of U.S. Provisional Application Nos. 60/219,283 and 60/246,186, filed Jul. 19, 2000 and Nov. 16, 2000 respectively.

STATEMENT REGARDING FEDERALLY SPONSORED RESEARCH

This invention was supported by the National Institutes of Health, Grant No. CA-78039. The United States government may have certain rights in this invention.

FIELD OF THE INVENTION

The present invention relates in general to anti-cancer agents and more specifically to synthetic analogs of the antimitotic marine natural product curacin A.

BACKGROUND OF THE INVENTION

Natural products remain a significant source of promising lead structures for drug development. Cragg, G. M.; Newman, D. J.; Snader, K. M. *J. Nat. Prod.* 1997, 60, 52; Shu, Y.-Z. *J. Nat. Prod.* 1998, 61, 1053; Nicolaou, K. C.; Vourloumis, D.; Winssinger, N.; Baran, P. S. *Angew. Chem., Int. Ed.* 2000, 39, 44. In recent years, an expansion of the structural diversity pool by preparation of libraries of natural products or natural product-like molecules has become a major focus of combinatorial chemistry. Tan, D. S.; Foley, M. A.; Shair, M. D.; Schreiber, S. L. *J. Am. Chem. Soc.* 1998, 120, 8565; Nicolaou, K. C.; Winssinger, N.; Vourloumis, D.; Oshima, T.; Kim, S.; Pfeffeirkorn, J.; Xu, J.-Y.; Li, T. *J. Am. Chem. Soc.* 1998, 120, 10814; Meseguer, B.; Alonso-Diaz, D.; Griebenow, N.; Herget, T.; Waldmann, H. *Angew. Chem., Int. Engl.* 1999, 19, 2902. After completion of the total synthesis of the strongly antimitotic Lyngbya majuscula metabolite curacin A in 1996 (Wipf, P.; Xu, W. *J. Org. Chem.* 1996, 61, 6556), the inventors remained intrigued by the impressive antiproliferative profile (Verdier-Pinard, P.; Sitachitta, M.; Rossi, J. V.; Sackett, D. L.; Gerwick, W. H.; Hamel, E. *Arch. Biochem. Biophys.* 1999, 370, 51; Gerwick, W. H.; Protear, P. J.; Nagle, D. G.; Hamel, E.; Blokhin, A.; Slate, D. *J. Org. Chem.* 1994, 59, 1243) of this marine natural product and its potential use as a lead structure for the development of new synthetic tubulin polymerization inhibitors. For a review of agents that interact with the mitotic spindle, see: Jordan, A.; Hadfield, J. A.; Lawrence, N. J.; McGown, A. T. *Med. Res. Rev.* 1998, 18, 259–69. For recent evaluations of small-molecule antimitotic agents, see: Haggarty, S. J.; Mayer, T. U.; Miyamoto, D. T.; Fathi, R.; King, R. W.; Mitchison, T. J.; Schreiber, S. L. *Chem. Biol.* 2000, 7, 275; Owa, T.; Okauchi, T.; Yoshimasa, K.; Sugi, N. H.; Ozawa, Y.; Nagasu, T.; Koyanagi, N.; Okabe, T.; Kitoh, K.; Yoshino, H. *Bioorg. Med. Chem. Lett.* 2000, 10, 1223; Uckun, F. M.; Mao, C.; Vassilev, A. O.; Navara, C. S.; Narla, K. S.; Jan, S.-T. *Bioorg. Med. Chem. Lett.* 2000, 10, 1015.

Compounds that inhibit cell proliferation are potentially useful in treating cancer, among other diseases. Curacin A is one such compound that inhibits cell growth and mitosis. See U.S. Pat. Nos. 6,057,348 and 5,324,739. Curacin A is believed to act by inhibiting microtubule processes associated with cell replication. It does this by binding to the colchicine-binding site, which is a relatively unique drug binding site.

Microtubules, the GTP hydrolysis-induced macromolecular assembly of $\alpha/\beta$ tubulin heterodimers, are an indispensable cytoskeletal component. Intracellular microtubule arrays serve as the scaffold for support of the endoplasmic reticulum and as the railway by which organelles and vesicles are delivered by motor proteins in interphase cells. Mitosis is a four-stage process of cell division resulting in the production two identical daughter cells from a single parent cell. Not only are the daughter cells identical to each other, they are identical to the parent cell.

At mitosis, microtubules also serve as the cables through which force generated by motor proteins causes sister chromatids to segregate. Agents that alter the formation, stability and/or disassembly of microtubules typically arrest cell growth at the $G_2/M$ interface of the cell cycle, and may therefore be useful as antitumor agents. There are three major drug-interactive sites on tubulin. Two of these are the basis of clinically useful antitumor agents. The paclitaxel site on $\beta$-tubulin is bound by paclitaxel and docetaxel, which stabilize microtubules against disassembly. The vinca domain, bound by agents such as vinblastine, vincristine and vinflurabine, which inhibit proper assembly of tubulin heterodimers into microtubules, is at an incompletely elucidated region of the heterodimer.

A third major class of microtubule perturbing agents bind to the colchicine site, which appears to be largely or exclusively on $\beta$-tubulin, but may include regions of the $\alpha/\beta$ interface. Agents that bind to the colchicine site appear to have affinity for unassembled $\alpha/\beta$ heterodimers. Until recently, all agents with known affinity for the colchicine site could be described as biaryl systems with appropriate substituents linked by short alkyl/alkenyl chains. The only useful pharmacological actions of colchicine site agents have been in the treatment of inflammatory processes. Discovery of the antitumor and associated antiangiogenesis actions in animal models of some colchicine site agents (e.g. 2-methoxyestradiol, combretastatin A-4 phosphate) suggest, however, that perturbation via this domain may yet prove useful for cancer treatment.

The discovery that curacin A and some of its closely related analogs bind the colchicine site with high avidity and are potent antimitotic agents caused a reevaluation of the biaryl systems theory. Early structure-activity relationship studies with curacins indicate that the parent structure is very intolerant of modification.

Curacin A exhibits anticancer properties similar to paclitaxel. Like paclitaxel, curacin A comes from a natural source. Both compounds exhibit a remarkable ability to disrupt cell mitosis, thereby inhibiting cell proliferation. This antimitotic ability makes these compounds potentially promising in treating cancer. In the case of both paclitaxel and curacin A, the trend is towards developing methods of synthesizing analogs that exhibit greater biological activity than the naturally derived compounds. Additionally, these methods should be more efficient than deriving the compounds from natural sources. As such, it is highly desirable to find ways of synthesizing more stable and biologically active analogs of curacin A.

According to several reports, curacin A promotes arrest of the cell cycle at the $G_2/M$ checkpoint and competitively inhibits the binding of [$^3$H]-colchicine to tubulin, and it can therefore be considered a colchicine site agent. Jordan, A.; Hadfield, J. A.; Lawrence, N. J.; McGown, A. T. *Med. Res. Rev.* 1998, 18, 259–69; Verdier-Pinard, P.; Lai, J.-Y.; Yoo, H.-D.; Yu, J.; Marquez, B.; Nagle, D. G.; Nambu, M.; White, J. D.; Falck, J. R.; Gerwick, W. H.; Day, B. W.; Hamel, E. *Mol. Pharmacol.* 1998, 53, 62. In addition to a large number of total syntheses of curacin A, the attractive biological properties of this compound have led to numerous biological studies. For discussion of curacin A syntheses, see: White, J. D.; Kim, T.-S.; Nambu, M. *J. Am. Chem. Soc.* 1995, 117, 5612; Hoemann, M. Z.; Agrios, K. A.; Aube, J. *Tetrahedron Lett.* 1996, 37, 935; Ito, H.; Imai, N.; Takao, K.; Kobayashi, S. *Tetrahedron Lett.* 1996, 37, 1799; Onada, T.; Shirai, R.; Koiso, Y.; Iwasaki, S. *Tetrahedron Lett.* 1996, 37, 4397; Lai, J.-Y.; Yu, J.; Mekonnen, B.; Falck, J. R. *Tetrahedron Lett.* 1996, 37, 7167; White, J. D.; Kim., T.-S.; Nambu, M. *J. Am. Chem. Soc.* 1997, 119, 103; Hoemann, M. Z.; Agrios, K. A.; Aube, J. *Tetrahedron* 1997, 53, 11087; Muir, J. C.; Pattenden, G.; Ye, T. Tetrahedron Lett. 1998, 39, 2861. However, even minor changes in the structure of curacin A can lead to essentially inactive derivatives. Verdier-Pinard, P.; Lai, J.-Y.; Yoo, H.-D.; Yu, J.; Marquez, B.; Nagle, D. G.; Nambu, M.; White, J. D.; Falck, J. R.; Gerwiek, W. H.; Day, B. W.; Hamel, E. *Mol. Pharmacol.* 1998, 53, 62; Marquez, B.; Verdier-Pinard, P.; Hamel, E.; Gerwick, W. H. *Phytochemistry,* 1998, 49, 2387; Nishikawa, A.; Shirai, R.; Koiso, Y.; Hashimoto, Y.; Iwasaki, S. *Bioorg. Med. Chem. Lett.* 1997, 7, 2657; Martin, B. K. D.; Mann, J.; Sageot, O. A. *J. Chem. Soc., Perkin Trans.* 1, 1999, 2455; Onoda, T.; Shirai, R.; Koiso, Y.; Iwasaki, S. *Tetrahedron* 1996, 52, 14543; Blokhin, A. V.; Yoo, H. D.; Geralds, R. S.; Nagle, D. G.; Gerwick, W. H.; Hamel, E. *Mol. Pharmacol.* 1995, 48, 523.

Critical issues, therefore, for further pharmaceutical development of any sufficiently active analog are increases in chemical stability, increases in hydrophilicity and improved availability versus the natural product. Curacin A is sensitive to oxidation, acids, and bases, and is readily, irreversibly absorbed into plastic containers such as polyethylene 96-well plates. Therefore, a need exists in the art for more efficient synthetic methods for producing curacin A analogs.

SUMMARY OF THE INVENTION

The present invention provides such methods. The present invention comprises the synthesis of 1-(un- and substituted aryl)-4-methyl-11-(heterocycle)undeca-4,6,10-trien-1-ols, and related compounds, and their preparation by a parallel and fluorous phase scheme. The lead compounds on which the idea for these agents was derived are structurally and synthetically complex antimitotic agents that suffer from physiochemical shortcomings (extreme hydrophobicity, easily oxidized to inactive species). The compounds of the present invention are both structurally and synthetically simpler and are not prone to oxidative inactivation. The compounds potently (in nanomolar concentrations) inhibit the growth of cultured human carcinoma cells, bind isolated tubulin and inhibit its assembly into microtubules in vitro, and cause mitotic block as determined by phosphorylation of histone H3 in human breast carcinoma cells.

DESCRIPTION OF THE DRAWINGS

The present invention will now be described, for purposes of illustration and not limitation, in conjunction with the following figures wherein.

DETAILED DESCRIPTION OF THE INVENTION

Figure 1:
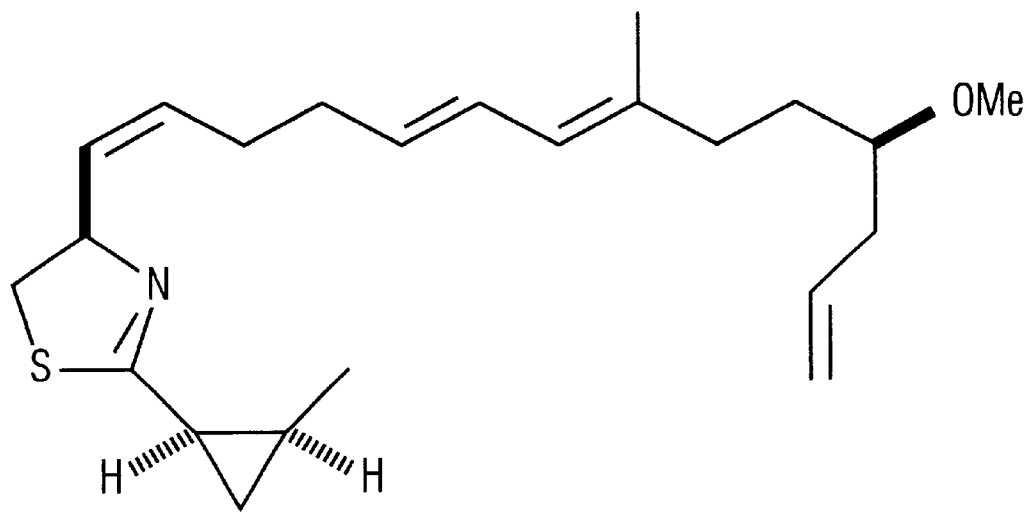
FIG. 1 depicts the structures of curacin A and colchicine.
Figure 1:
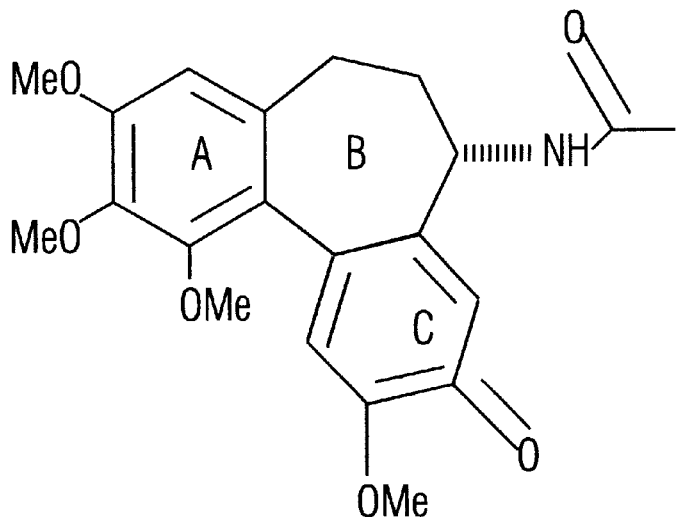

The present invention will now be described for the purposes of illustration and not limitation. The references cited in this detailed description of the present invention, to the extent that they provide exemplary procedural or other details supplementary to those set forth herein, are specifically incorporated herein by reference. Because curacin A binds to the colchicine site on tubulin, and the alkenyl thiazoline moiety in curacin A is believed by those in the art to be largely responsible for the chemical instability of the natural product, the inventors substituted the heterocycle with electron-rich aromatics reminiscent of the A-ring in colchicine, as shown in FIG. 1. The homoallylic methyl ether terminus of curacin A was substituted with a broad range of more hydrophilic benzylic alcohols while maintaining the diene spacer unit, which has proven to be essential in the limited structure-activity relationship studies of curacin A published to date. Verdier-Pinard, P.; Sitachitta, M.; Rossi, J. V.; Sackett, D. L.; Gerwick, W. H.; Hamel, E. *Arch. Biochem. Biophys.* 1999, 370, 51; Gerwick, W. H.; Protear, P. J.; Nagle, D. G.; Hamel, E.; Blokhin, A.; Slate, D. *J. Org. Chem.* 1994, 59, 1243; Verdier-Pinard, P.; Lai, J.-Y.; Yoo, H.-D.; Yu, J.; Marquez, B.; Nagle, D. G.; Nambu, M.; White, J. D.; Falck, J. R.; Gerwick, W. H.; Day, B. W.; Hamel, E. *Mol. Pharmacol.* 1998, 53, 62; Marquez, B.; Verdier-Pinard, P.; Hamel, E.; Gerwick, W. H. *Phytochemistry,* 1998, 49, 2387; Nishikawa, A.; Shirai, R.; Koiso, Y.; Hashimoto, Y.; Iwasaki, S. *Bioorg. Med. Chem. Lett.* 1997, 7, 2657; Martin, B. K. D.; Mann, J.; Sageot, O. A. *J. Chem. Soc., Perkin Trans.* 1, 1999, 2455; Onoda, T.; Shirai, R.; Koiso, Y.; Iwasaki, S. *Tetrahedron* 1996, 52, 14543; Blokhin, A. V.; Yoo, H. D.; Geralds, R. S.; Nagle, D. G.; Gerwick, W. H.; Hamel, E. *Mol. Pharmacol.* 1995, 48, 523.

Figure 2:
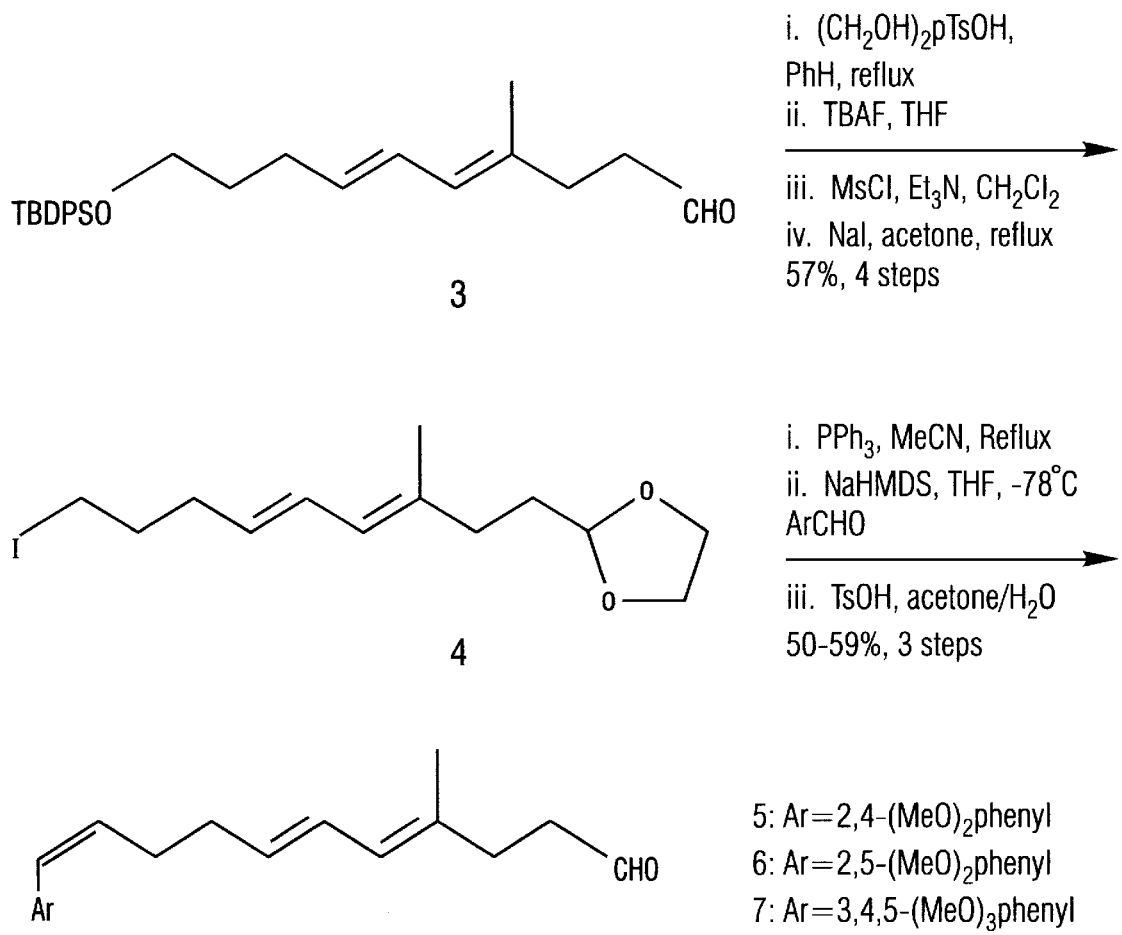
FIG. 2 illustrates the first part of the synthesis of 1-(un- and substituted aryl)-4-methyl-11-(heterocycle)undeca-4,6, 10-trien-1-ols.

Accordingly, three key building blocks 5–7, as shown in FIG. 2, were prepared by standard solution synthesis from the readily available aldehyde 3, also shown in FIG. 2. Wipf, P.; Xu, W. *J. Org. Chem.* 1996, 61, 6556. After protection with ethylene glycol, desilylation, and mesylation, Finkelstein reaction with sodium iodide produced dioxane (as shown by 4 in FIG. 2) in 57% yield. The corresponding Wittig reagent was condensed with 2,4-dimethoxy-, 2,5-dimethoxy-, and 3,4,5-trimethoxybenzaldehyde, respectively, to give the aldehydes 5–7 in 50–59% overall yields from 4 after acetal cleavage. Aldehydes 5–7 were obtained as all-(E) isomers at the diene moiety in an approximately 5:1 ration of (Z):(E) alkene stereoisomers after the Wittig condensation and were characterized by $^1$H NMR and HRMS.

Figure 3:
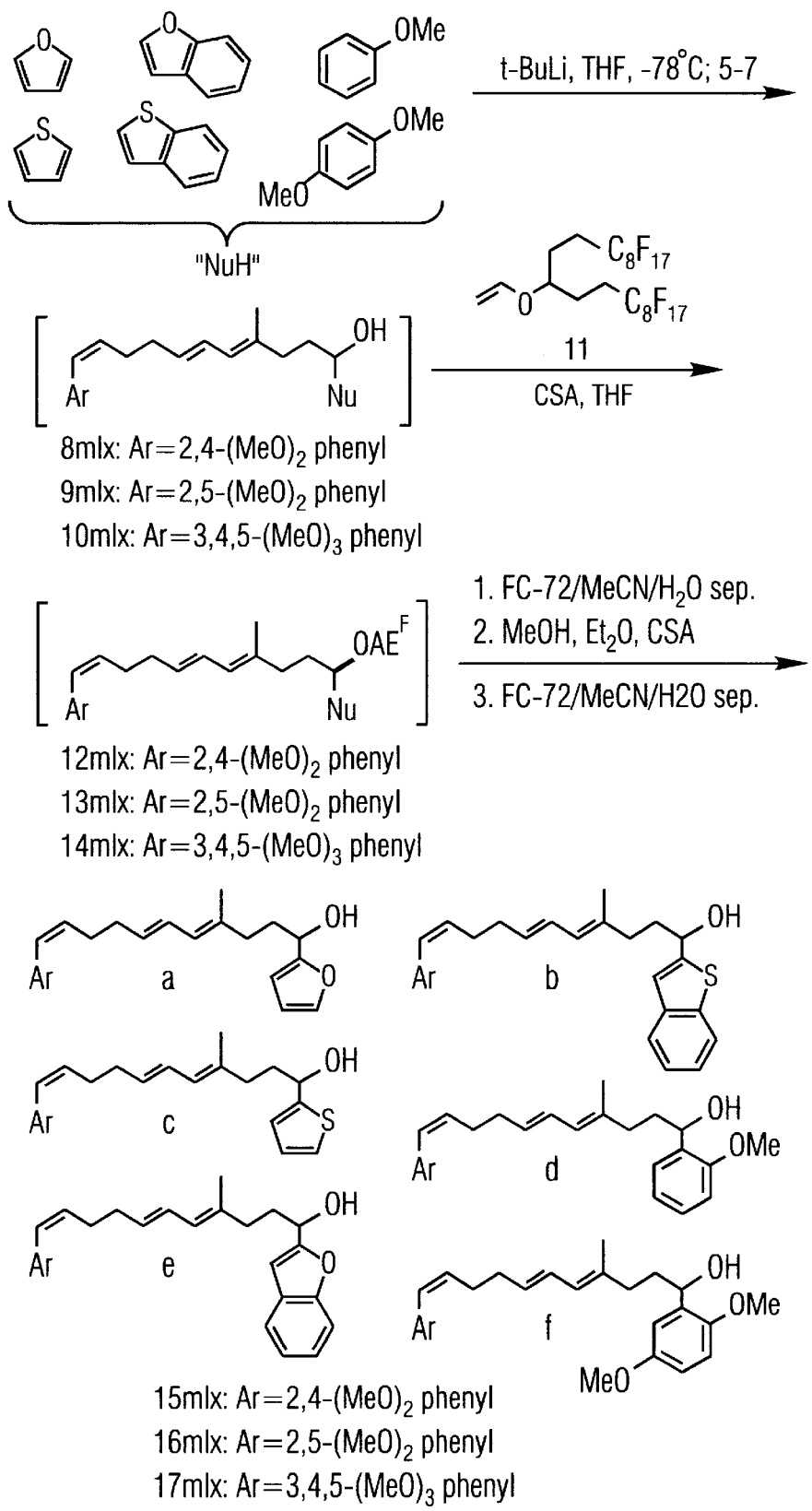
FIG. 3 illustrates the second part of the synthesis of 1-(un- and substituted aryl)-4-methyl-11-(heterocycle)undeca-4,6, 10-trien-1-ols.
Figure 4:
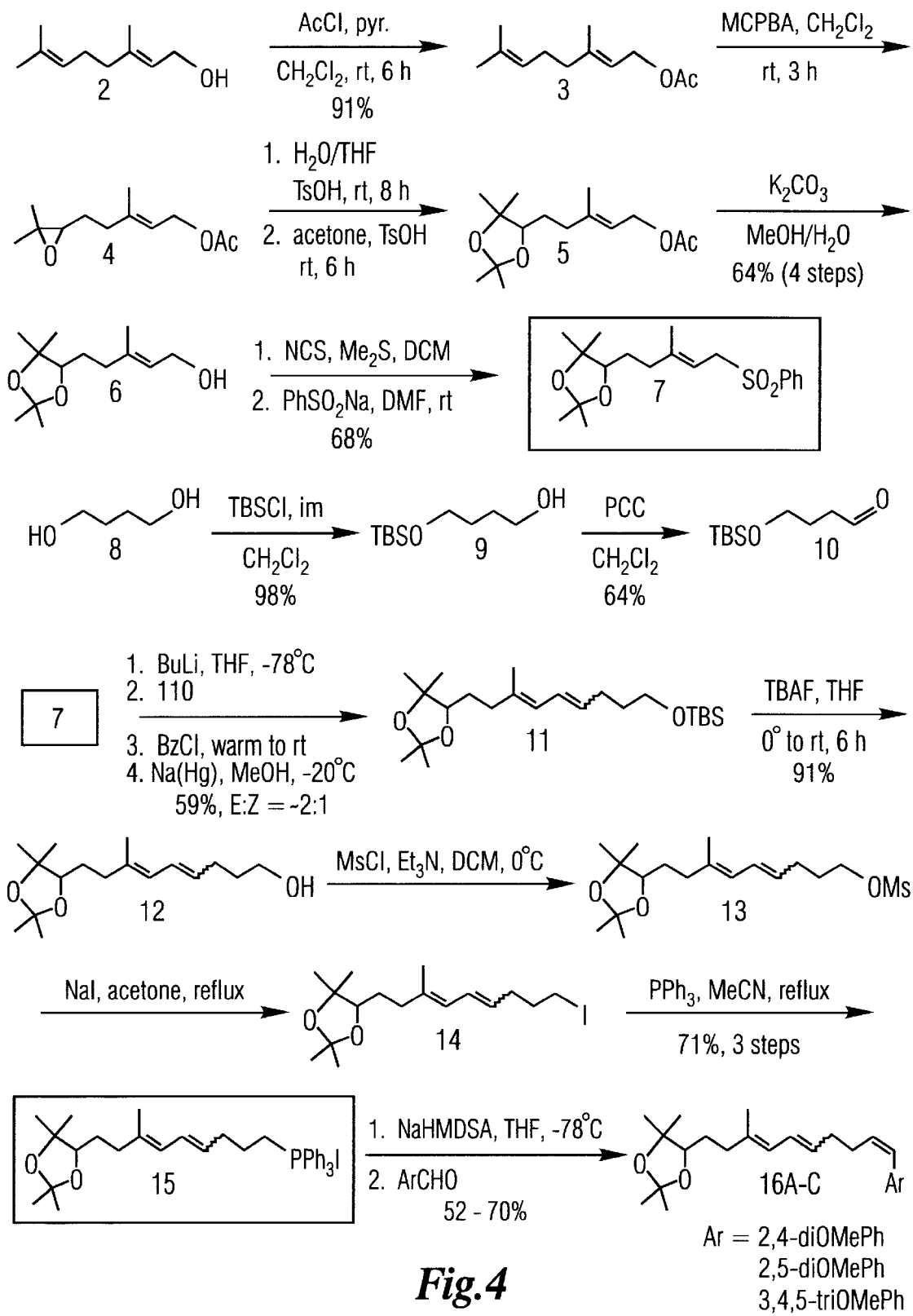
FIG. 4 shows the synthesis of the dioxolane intermediates.
Figure 5:
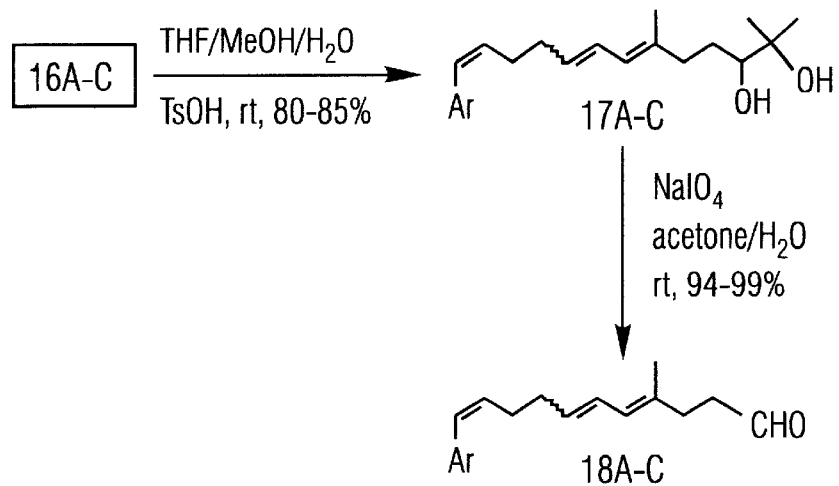
FIG. 5 demonstrates the synthesis of the aldehyde intermediates.
Figure 6:
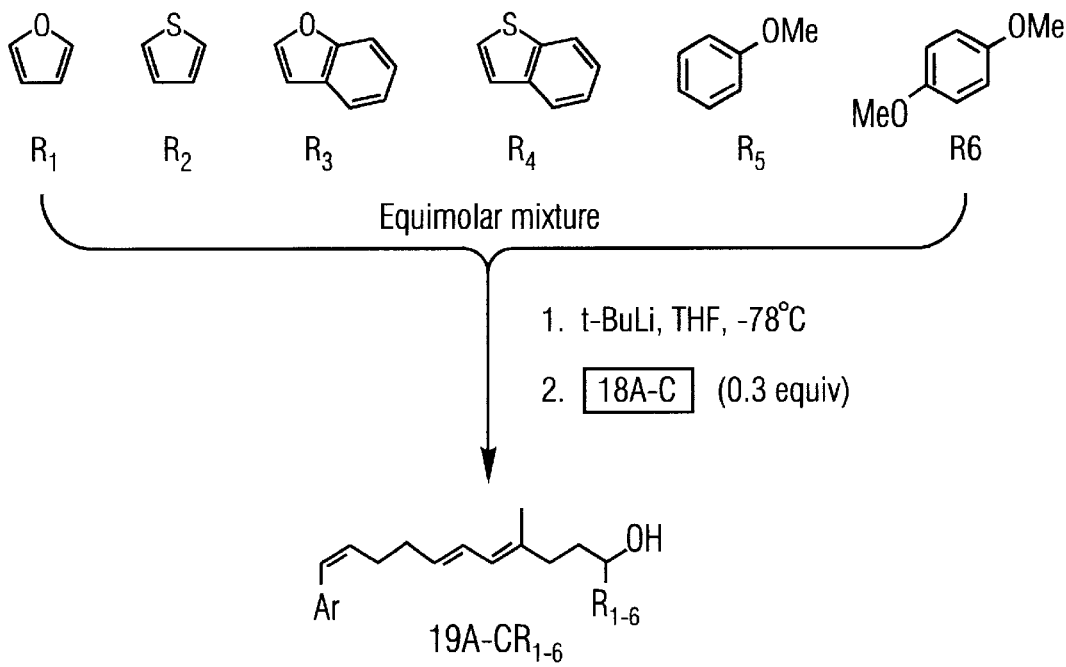
FIG. 6 depicts the synthesis of the targets.
Figure 7:
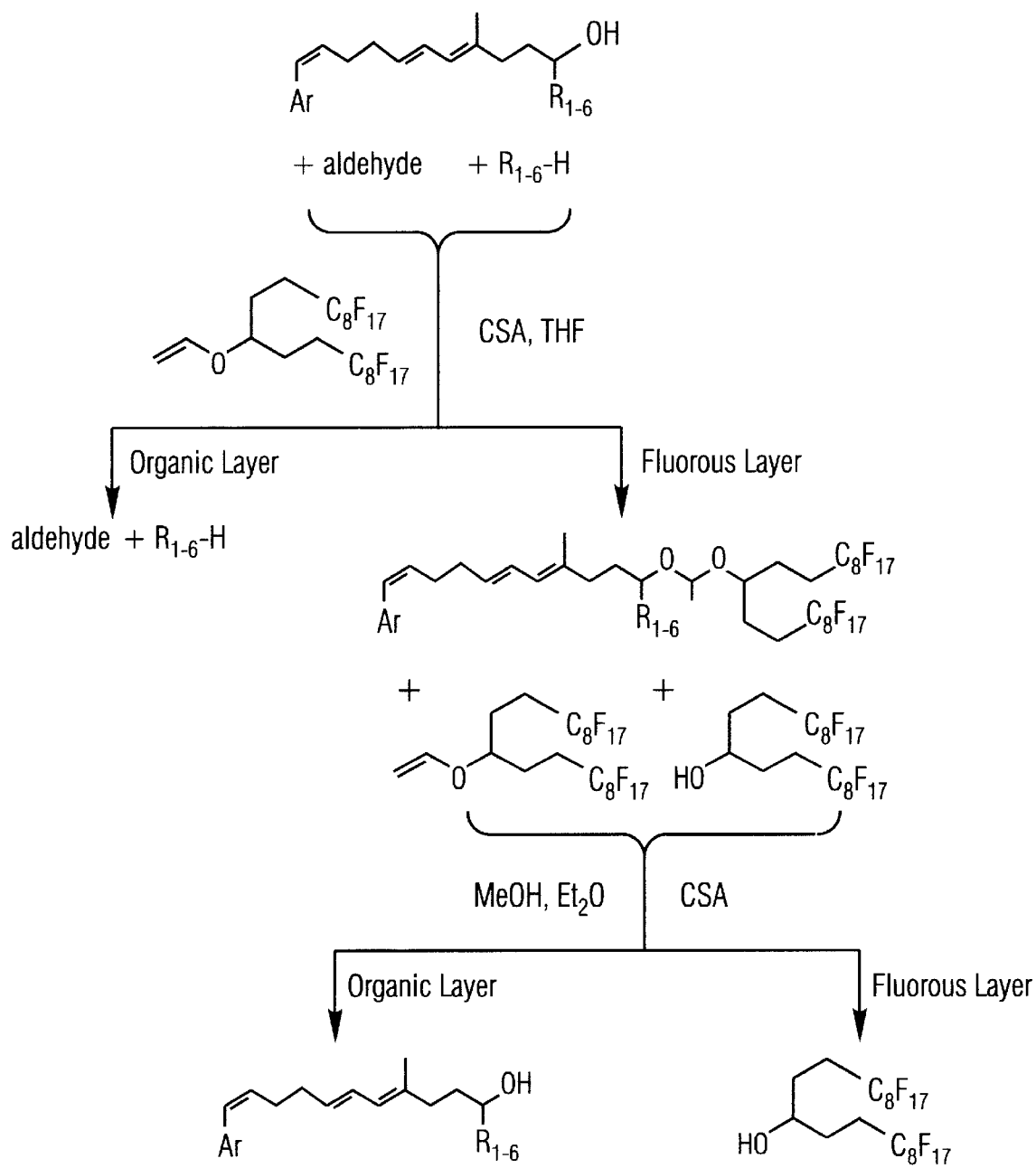
FIG. 7 illustrates the florous purification of the targets.

Solution phase combinational synthesis of mixtures for biological screening is not a commonly used technique, but the inventors herein believe it represents an efficient approach for rapid lead evaluation if the composition of the mixture is clearly defined and the throughput of the assay is limited. Boger, D. L.; Lee, J. K.; Goldberg, J.; Jin, Q. *J. Org. Chem.* 2000, 65, 1467; Houghten, R. A.; Pinilla, C.; Appel, J. R.; Blondelle, S. E.; Dooley, C. T.; Eichler, J.; Nefzi, A.; Ostresh, J. M. *J. Med. Chem.* 1999, 42, 3743; Nazarpack-Kandlousy, N.; Zweigenbaum, J.; Henion, J.; Eliscev, A. V. *J. Comb. Chem.* 1999, 1 ,199. To establish the validity of the inventors' analog design, seven mixtures of six to nine compounds each were prepared by exposure of 5–7 as well as derivatives with other aryl substituents to a cocktail of three to six aryllithium reagents. The most biologically active mixtures were obtained from reaction of 5–7 with 2-lithiated furan, thiophene, benzofuran, benzothiophene, anisole and 1,4-dimethoxybenzene as shown in FIG. 3. The lithiation was performed directly on the mixture and was heteroatom-directed. Because a large excess (3 equiv. each) of organolithium reagents in a 1:1:1:1:1:1 ratio was used to ensure fast and unselective aldehyde addition, the resulting alcohols 8mix–10mix were heavily contaminated with excess Nu-H after aqueous workup. Fluorous quenching of the crude product with an excess of the recently developed vinyl ether 11 provided a convenient means to ensure rapid and thorough purification. Wipf, P.; Reeves, J. T. *Tetrahedron Lett.* 1999, 40, 5139; Studer, A.; Hadida, S.; Ferritto, R.; Kim, S.-Y.; Jeger, P.; Wipf, P.; Curran, D. P. *Science* 1997, 275, 823; Curran, D. P. *Agnew. Chem., Int. Ed.* 1998, 37, 1174.

Following a simple liquid/liquid extraction with a mixture of the perfluorinated solvent FC-72 and MeCN/H$_2$O, the partially fluorinated acetals 12mix–14mix were collected in the FC-72 layer. Organic impurities remained in the organic phase and inorganic salts preferred the aqueous environment. Methanolysis of the fluorous extract and renewed post-reaction fluorous/organic/aqueous liquid-liquid extraction yielded pure 6-component mixtures 15mix–17mix in the organic phase. The three mixtures were characterized by LC-MS using a reverse-phase (C18) column and positive ionization electrospray mass spectral detection as well as by LC NMR. Each mixture contained the six expected products in close-to-equimolar ration, with minor amounts (approximately 15–20%) of the (E)-alkene derivatives from the Wittig reaction. No organic impurities >5% were detected. The fluorous phase contained the solvolysis products of protective group 11.

Samples of 15mix–17mix were screened for biological activity. The biochemical and cell growth activity of 15mix–17mix is summarized in Table I below. Each of the mixtures inhibited by >50% the 30° C. GTP-induced polymerization of glutamate-containing isolated bovine brain tubulin, as shown in Tables I and II, at concentrations<5 $\mu\mu$M (summed concentration based on average molecular weight of the components), with both 16mix and 17mix showing high potency. Tubulin without microtubule-associated proteins was prepared from fresh bovine brains (Hamel, E.; Lin, C. M. *Biochemistry* 1984, 23, 4173). Reactions were carried out as described previously. Verdier-Pinard, P.; Lai, J.-Y.; Yoo, H.-D.; Yu, J.; Marquez, B.; Nagle, D. G.; Nambu, M.; White, J. D.; Falck, J. R.; Gerwick, W. H.; Day, B. W.; Hamel, E. *Mol. Pharmacol.* 1998, 53, 62.

Briefly, tubulin (final concentration 10 $\mu$M; 1 mg/mL) was preincubated with drugs dissolved in DMSO (4% v/v final concentration) and monosodium glutamate (0.8 M final concentration) for 15 minutes at 30° C. The reaction mixture was cooled to 0° C. and GTP (1 mM final concentration) was added. Reaction mixtures were transferred to cuvettes at 0° C. in a Beckman-Coulter 7400 spectrophotometer reading absorbance at 350 nm. Baselines at 0° C. were established and the temperature was quickly raised to 30° C. (in approximately 1 min. with an electronically controlled Peltier temperature controller). The change in absorbance 20 minutes after samples reached 30° C. was used to calculate the extent of polymerization. The change in absorbance at this time point for vehicle plus no GTP was considered 100% assembly inhibition, while the change in absorbance for GTP plus vehicle was taken as 0% inhibition. Each series of determination included positive and negative control determinations plus one determination made with 5 $\mu$M curacin A.

Assays to determine whether 15mix–17mix inhibited binding of [$^3$H]colchicine to tubulin at both 30° C. and 37° C. were performed. This was accomplished using methods described previously. Kang, G.-J.; Getahun, Z.; Muzaffar, A.; Brossi, A.; Hamel, E. *J. Biol. Chem.* 1990, 265, 10255; Verdier-Pinard, P.; Lai, J.-Y.; Yoo, H.-D.; Yu, J.; Marquez, B.; Nagle, D. G.; Nambu, M.; White, J. D.; Falck, J. R.; Gerwick, W. H.; Day, B. W.; Hamel, E. *Mol. Pharmacol.* 1998, 53, 62. Briefly, 5 $\mu$M [$^3$H]colchicine (2.3 TBq/mmol), drug (1, 5, 10, 50, or 250 $\mu$M), or vehicle (DMSO, 5% v/v) were incubated at 30° C. for 15 minutes or at 37° C. for 10 minutes with 1 $\mu$M tubulin in the presence of 1 M monosodium glutamate, 0.1 M glucose-1-phosphate, 1 mM MgCl$_2$, 1 mM GTP, and 0.5 mg/mL bovine serum albumin. The solutions were filtered through two stacks of DEAE-cellulose filters and the radioactivity in the filtrate was determined by scintillation spectrometry. Each series of determinations included positive controls of 1, 5, and/or 50 $\mu$M curacin A.

As can be appreciated by reference to Table I, the assays showed both 15mix and 16mix were significantly weaker at displacement than curacin A, whereas one or more of the components comprising 17mix had significant concentration-dependent inhibitory activity at the colchicine site. Screening for growth inhibitory activities against a short series of human breast, prostate and ovarian carcinoma cells confirmed the trends seen in the biochemical screens and, moreover, showed that 17mix inhibited cell proliferation at submicromolar concentrations.

The screening for growth inhibitory activities involved plating cells (500–2000 cells/well depending on the cell line) in 96-well plates and allowing them to attach and grow for 72 hours. The cells were then treated with vehicle (DMSO) or drug [50, 10, 2, 0.4, and 0.08 $\mu$M (for the mixtures, these were the summed, apparent concentrations, i.e., approximately six times the concentration of each compound); 10, 2, 0.4, 0.08, and 0.16 $\mu$M for curacin A; then 1, 0.2, 0.04, 0.008, and 0.0016 $\mu$M for 17a–e and curacin A] for the given times. One plate consisted entirely of cells used for a time zero cell number determination. The other plates contained eight wells of control cells, eight wells of medium, and each drug concentration tested in quadruplicate. Cell numbers were obtained spectrophotometrically (absorbance at 490 nm minus that at 630 nm) in a Dynamax plate reader after treatment with 3-(4,5-dimethylthiazol-2-yl)-5-(3-carboxymethoxyphenyl)-2-(4-sulfophenyl)-2H-tetrazolium (MTS.; Owen's reagent) using N-methyldibenzopyurazine methyl sulfate (phenazine methosulfonate) as the electron acceptor.

Because of the intriguing activities in the tubulin polymerization and g inhibition assays observed for the 17mix, the components of 17a–f were synthesized individually to determine their specific potencies. The synthesis of 17a–f proceeded as shown in FIGS. 2 and 3, but the final products were purified by column chromatography and were characterized by $^1$H and $^{13}$C NMR, IR, and HRMS. As a negative control, single compounds of 15mix were also resynthesized, and biological testing confirmed their lack of activity. Analysis of the discrete compounds revealed that four of them, 17b–e, showed considerable potencies in all of the isolated protein and cell-based growth inhibition screens, and the 1-(2,5-dimethoxyphenyl)-containing 17f was essentially inactive, as shown in the Table I. The furan-containing 17a, although potent in the tubulin assays and against the breast carcinoma cell line, exhibited reduced antiproliferative activity against the prostate and ovarian carcinoma cells. As comparison of 17mix with 17a–f clearly demonstrates, tubulin polymerization and cellular growth inhibition reflect the sum of the individual compounds that make up 17mix. The inventors believe such results validate the mixture-based screening strategy. In contrast, colchicine-binding inhibition for 17mix does not correlate as well with the activity of 17a–f, possibly due to combination of high-affinity (colchicine-site) and other low-affinity binding sites on tubulin for these compounds. Some less active curacin A analogs actually enhance the binding of [$^3$H]colchicine to tubulin.

Further verification of the biological activity of compounds 17a–e was obtained in living tumor cells by quantifying their effect on mitotic index, essentially, counting the number of cells in the mitotic phase of the cell cycle. Antimitotic compounds increase the mitotic index, which can be quantified immunohistochemically using an antibody to a mitosis-specific phosphorylated core histone protein. MCF-7 human breast carcinoma cells were treated with increasing concentrations of compounds 17a–e (7.8–1000 nM), curacin A (3.1–400 nM), and vinblastine (0.08–10 nM) for 14–16 hours. The morphology of the cellular nuclei and the mircrotubule cytoskeleton, as well as the phosphorylation of a core histone protein, were visualized using a multiparameter immunofluorescence approach. For example, compound 17b induced a large increase in the fraction of cells exhibiting condensed chromatin and increased core histone phosphorylation. Compound 17b induced cell rounding and the generalized loss of structured microtubules in the same cells. The mitotic index in drug-treated cells was measured. To assess the relative activity of compounds 17a–e and two known microtubule disrupting drugs, vinblastine and curacin A, the minimum effective concentration of each drug was measured. Compounds 17a–d were the most potent of the new agents with minimum effective concentrations in the submircomolar range and well within an order of magnitude of the activity of parent ciracin A.

Phosphorylation of histone H3 occurs during mitosis and is linked to chromosome condensation. Thus, antimitotic agents cause an accumulation of cells containing phospho-He. Wei, Y.; Mizzen, C. A.; Cook, R. G.; Gorovsky, M. A.; Allis, C. D. *Proc. Natl Acad. Sci. USA* 1998, 95, 7480. MCF-7 human breast carcinoma cells were treated with increasing concentrations (0.0075–15 µM) of 17mix and 17a–e for 14 hours and mitotic index quantities automatically. Presented in the Table II below, vehicle (DMSO) treated cells showed a mitotic index in the range of 4–8% consistent with the range found for normal cycle cells. Vinblastine, a classic mitotic inhibitor, was tested over a range of 0.49 nM to 0.1 µM and caused a maximum accumulation of adherent cells in mitosis of 26%. Compounds od 17c and 17e were the most potent of the new agents, causing maximum mitotic block at sub-micromolar concentrations.

TABLE 1

50% Cochicine Binding Inhibitory Concentration (CBI), 50% Tubulin Polymerization Inhibition Concentration (TPI), and 50% Growth Inhibitory Concentrations (GI$_{50}$) for 15mix–17mix and Discrete Compounds Comprising 17mix.

| | CBI$^a$ (µM) | | | TPI$^b$ | GI$_{50}$ (µM)$^c$ | | |
|---|---|---|---|---|---|---|---|
| | | | | MDA$^d$-MB231 | PC-3$^e$ | 2008$^f$ |
| Compound | 30° C. | 37° C. | IC$_{50}$ (µM) | (48 h) | (48 h) | (48 h) |
| 15mix | >250 | >250 | 4 | >50 | >50 | 36 ± 5 |
| 16mix | >50 | 48 ± 5 | 2 | 5.2 ± 2 | >50 | 21 ± 4 |
| 17mix | >50 | 26 ± 6 | 1.4 | 0.30 ± 0.1 | 0.80 ± 0.5 | 0.58 ± 0.2 |
| 17a | 32 ± 4 | 9 ± 6 | 0.9 | 0.69 ± 0.1 | 8.0 ± 4 | 2.7 ± 1 |
| 17b | 9 ± 7 | 19 ± 2 | 1.4 | 0.23 ± 0.06 | 0.62 ± 0.05 | 0.36 ± 0.001 |
| 17c | 39 ± 10 | 9 ± 3 | 1.2 | 0.28 ± 0.04 | 0.38 ± 0.08 | 0.28 ± 0.02 |
| 17d | 9 ± 5 | 9 ± 4 | 1.2 | 0.34 ± 0.03 | 0.62 ± 0.2 | 0.33 ± 0.02 |
| 17e | 9 ± 4 | 28 ± 8 | 1.6 | 0.12 ± 0.07 | 0.31 ± 0.2 | 0.27 ± 0.05 |
| 17f | >50 | >50 | >50 | 9.7 ± 1 | >50 | 22 ± 5 |
| curacin A | 0.9 ± 0.3 | 0.6 ± 0.1 | 0.78±0.07 | 0.096 ± 0.06 | 0.050 ± 0.009 | 0.035 ± 0.007 |

$^a$Values shown are means (N – 9 over four concentrations) ± standard deviations (SD) for incubation at 30° C. for 15 minutes and 37° C. for 10 minutes.
$^b$Average of two determinations except for curacin A, where N = 7 (± SD).
$^c$Means (N = 4 over 10 concentrations) ± SD.
$^d$MDA is a line of breast cancer cells.
$^e$PC3 is a line of prostate cancer cells.
$^f$2008 is a line of ovarian cancer cells.

TABLE II

Percent Colchicine Binding Inhibition (CBI), Tubulin Polymerization Inhibition (TPI), and 50% Growth Inhibitory Concentration ($GI_{50}$) for Target Mixtures and Discretes (re-test values in parentheses).

| Compd | CBI 1 μM | CBI 5 μM | CBI 50 μM | TPI 5 μM | MDA 48 h | MDA 96 h |
|---|---|---|---|---|---|---|
| $19AR_{1-6}$ | −7.1 ± 6.5 | 20.0 ± 7.2* | −37.4 ± 10.9* | 52.5 | >50 | 16.9 ± 15.2 |
| $19AR_1$ | −4.6 ± 8.5 | −2.2 ± 8.2 | 13.2 ± 12.7 | 81.7 | 26.8 ± 0.9 | 3.26 ± 6.13 |
| $19AR_2$ | −0.7 ± 7.5 | −2.7 ± 6.5 | −31.7 ± 7.8* | 51.8 | 24.0 ± 1.2 | 7.18 ± 4.67 |
| $19AR_3$ | 0.7 ± 16.2 | −50.0 ± 12.7* | −29.0 ± 9.2* | 60.4 | 42.1 ± 1.4 | 6.43 ± 7.42 |
| $19AR_4$ | 1.4 ± 18.5 | −41.0 ± 17.8* | −26.4 ± 14.7* | 60.5 | >50 | 18.6 ± 3.0 |
| $19AR_5$ | −3.4 ± 3.2 | −17.4 ± 7.9* | −26.1 ± 11.5* | 34.2 | >50 | 15.3 ± 9.8 |
| $19AR_6$ | 1.7 ± 13.9 | −6.8 ± 13.1 | −22.8 ± 8.9* | 31.2 | 39.3 ± 11.3 | 18.3 ± 13.6 |
| $19BR_{1-6}$ | 1.6 ± 21.2 | 6.1 ± 38.1 (5.3 ± 8.4) | 26.1 ± 63.* (12.6 ± 2.8*) | 79.0 | 5.19 ± 1.98 | 3.44 ± 0.89 |
| $19CR_{1-6}$ | 7.8 ± 11.3 | 19.5 ± 9.0* (−0.7 ± 5.9) | 32.3 ± 7.3* (38.4 ± 2.2*) | 80.8 | 0.304 ± 1.096 | 0.481 ± 0.084 |
| $19CR_1$ | | 30.3 ± 7.5* | 59.7 ± 1.6* | 94.4 | 0.288 ± 0.166 | 0.790 ± 0.167 |
| $19CR_2$ | | 30.2 ± 7.3* | 71.6 ± 2.8* | >100 | 0.083 ± 0.125 | 1.28 ± 0.12 |
| $19CR_3$ | | 9.9 ± 3.0 | 59.0 ± 7.5* | >100 | 0.151 ± 0.051 | 0.214 ± 0.051 |
| $19CR_4$ | | 5.0 ± 7.4 | 73.0 ± 2.4* | >100 | 0.243 ± 0.046 | 0.221 ± 0.033 |
| $19CR_5$ | | 12.5 ± 8.1 | 68.7 ± 1.1* | 74.6 | 0.086 ± 0.146 | 0.204 ± 0.046 |
| $19CR_6$ | | 0.7 ± 6.0 | 20.3 ± 4.8* | 3.5 | 9.70 ± 1.32 | 8.73 ± 0.05 |
| curacin A | | 84.9 ± 1.07* (95.0 ± 0.7*) | 96.2 ± 0.7* (97.7 ± 0.0*) | 97.9 | 0.186 ± 0.226 | 0.064 ± 0.007 |

| Compd | $GI_{50}$ PC3 48 h | $GI_{50}$ PC3 96 h | 2008 48 h | 2008 96 h |
|---|---|---|---|---|
| $19AR_{1-6}$ | >50 | >50 | 36.0 ± 5.2 | 22.8 ± 9.1 |
| $19AR_1$ | >50 | >50 | 20.2 ± 2.0 | 19.1 ± 3.1 |
| $19AR_2$ | >50 | 37.3 ± 6.5 | 23.8 ± 1.1 | 25.9 ± 2.1 |
| $19AR_3$ | >50 | 49.1 ± 8.9 | 12.2 ± 2.7 | 17.7 ± 2.7 |
| $19AR_4$ | >50 | >50 | 29.8 ± 1.4 | 26.9 ± 3.0 |
| $19AR_5$ | >50 | >50 | 30.8 ± 8.7 | 24.2 ± 3.9 |
| $19AR_6$ | >50 | >50 | 35.2 ± 2.4 | 32.9 ± 3.7 |
| $19BR_{1-6}$ | >50 | >50 | 21.2 ± 4.0 | 7.25 ± 5.00 |
| $19CR_{1-6}$ | <0.08 | 1.39 ± 0.22 | 0.577 ± 0.169 | 0.928 ± 0.058 |
| $19CR_1$ | 7.99 ± 3.52 | 7.73 ± 1.22 | 2.72 ± 0.96 | 2.53 ± 0.64 |
| $19CR_2$ | 0.875 ± 1.024 | 1.22 ± 0.22 | 0.380 ± 0.002 | 0.235 ± 0.021 |
| $19CR_3$ | 0.366 ± 0.157 | 1.02 ± 0.38 | 0.311 ± 0.063 | 0.279 ± 0.030 |
| $19CR_4$ | 0.933 ± 1.249 | 0.634 ± 0.397 | 0.314 ± 0.025 | 0.268 ± 0.046 |
| $19CR_5$ | 0.596 ± 1.247 | 1.12 ± 0.04 | 0.204 ± 0.112 | 0.199 ± 0.036 |
| $19CR_6$ | >50 | >50 | 22.2 ± 4.9 | 22.1 ± 2.8 |
| curacin A | 0.050 ± 0.009 | 0.048 ± 0.008 | 0.035 ± 0.007 | 0.026 ± 0.012 |

*Significantly different from control, $p < 0.005$ (Student's t test).

TABLE III

Percent Colchicine Binding Inhibition (CBI) and Tubulin Polymerization Inhibition (TPI), and 50% Cancer Cell Growth Inhibitory Concentrations ($GI_{50}$).

| Compound | % CBI 5 μM, 37° C. (30° C.) | % CBI 50 μM, 37° C. (30° C.) | % TPI 5 μM | MDA-MB231 (breast) 48 h | MDA-MB231 (breast) 96 h | $GI_{50}$ (μM) PC3 (prostate) 48 h | PC3 (prostate) 96 h | 2008 (ovarian) 48 h | 2008 (ovarian) 96 h |
|---|---|---|---|---|---|---|---|---|---|
| JRC1 | 0 ± 7 (14 ± 5) | 87 ± 1 (80 ± 1) | 0 | 1.8 ± 0.3 | 4.1 ± 1.1 | 6.2 ± 1.3 | 8.8 ± 0.8 | 0.45 ± 0.50 | 3.7 ± 1.5 |
| JRC2 | 0 ± 17 (7 ± 5) | −52 ± 14 (7 ± 6) | 51 | 36 ± 22 | >50 | >50 | >50 | >50 | >50 |
| JRC3 | −35 ± 15 (35 ± 4) | 13 ± 12 (63 ± 6) | 100 | 0.20 ± 0.11 | 0.27 ± 0.16 | 0.13 ± 0.08 | 0.061 ± 0.059 | 0.22 ± 0.09 | 0.18 ± 0.11 |
| JRC4 | −21 ± 16 (38 ± 2) | 5 ± 13 (43 ± 19) | 100 | 0.32 ± 0.20 | 0.25 ± 0.02 | 0.24 ± 0.07 | 0.45 ± 0.09 | 0.30 ± 0.17 | 0.25 ± 0.05 |
| JRC5 | 1 ± 12 (9 ± 6) | −89 ± 7 (−220 ± 16) | 29 | 14 ± 3 | 5.8 ± 3.6 | 30 ± 6 | 28 ± 1 | 17 ± 3 | 23 ± 2 |
| JRoxime1 | 53 ± 2.2 (48 ± 12) | 37 ± 8 (57 ± 15) | 100 | 0.12 ± 0.10 | 0.38 ± 0.20 | 0.25 ± 0.8 | 0.53 ± 0.39 | 0.24 ± 0.18 | 0.34 ± 0.29 |
| JRoxime2 | −49 ± 25 (−9 ± 12) | −107 ± 18 (−1 ± 4) | 26 | 0.98 ± 0.20 | 15 ± 5 | 1.2 ± 1.9 | 8.8 ± 4.1 | 9.9 ± 8.7 | 39 ± 32 |
| JRoxime3 | −30 ± 6 (−10 ± 10) | −30 ± 7 (18 ± 6) | 3 | >50 | >50 | >50 | >50 | >50 | >50 |

TABLE III-continued

Percent Colchicine Binding Inhibition (CBI) and Tubulin Polymerization Inhibition (TPI), and 50% Cancer Cell Growth Inhibitory Concentrations (GI$_{50}$).

| | % CBI | | | | | $GI_{50}$ ($\mu$M) | | | |
| | 5 $\mu$M, 37° C. | 50 $\mu$M, 37° C. | % TPI | MDA-MB231 (breast) | | PC3 (prostate) | | 2008 (ovarian) | |
| Compound | (30° C.) | (30° C.) | 5 $\mu$M | 48 h | 96 h | 48 h | 96 h | 48 h | 96 h |
| --- | --- | --- | --- | --- | --- | --- | --- | --- | --- |
| JRCPOX | −8 ± 11 (−142 ± 59) | −74 ± 19 (−205 ± 17) | 83 | 18 ± 4 | 24 ± 0 | 49 ± 1 | 24 ± 1 | 18 ± 4 | 23 ± 1 |
| 345ket | −46 ± 3 (4 ± 8) | −59 ± 8 (7 ± 5) | 0 | 33 ± 2 | 28 ± 4 | >50 | >50 | >50 | >50 |
| JR DCCA | −39 ± 7 (9 ± 5) | −62 ± 5 (−12 ± 9) | 0 | >50 | >50 | >50 | >50 | >50 | >50 |
| curacin A | 87 ± 9 (78 ± 2) | 97 ± 0 (99 ± 1) | 98 | | | | | | |

Figure 8:
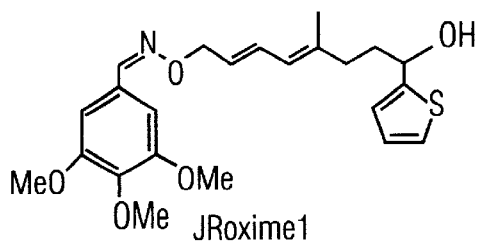
FIG. 8 depicts the structures of the JR compounds.
Figure 8:
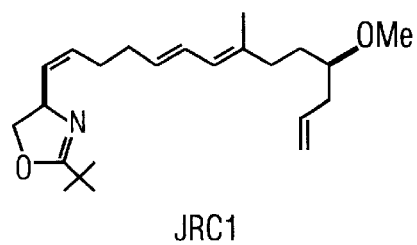
Figure 8:
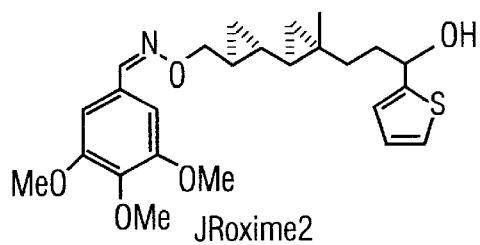
Figure 8:
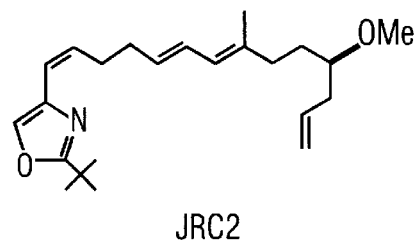
Figure 8:
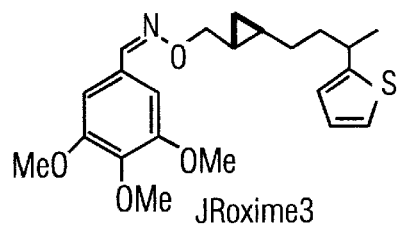
Figure 8:
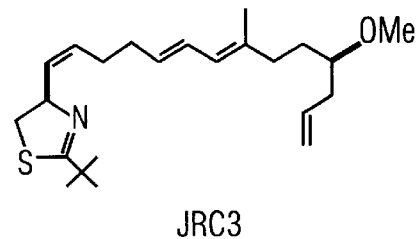
Figure 8:
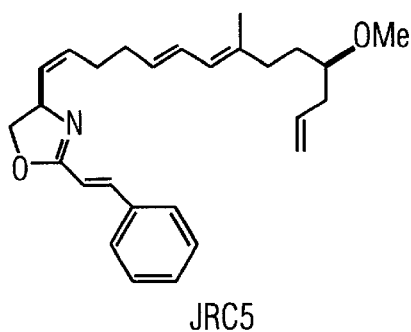
Figure 8:
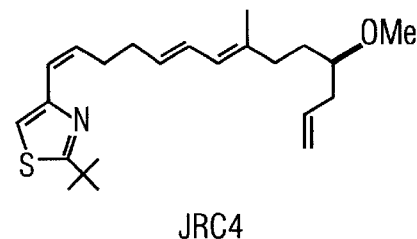
Figure 8:
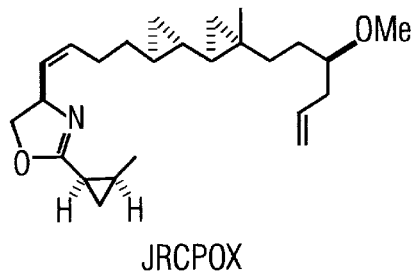
Figure 8:
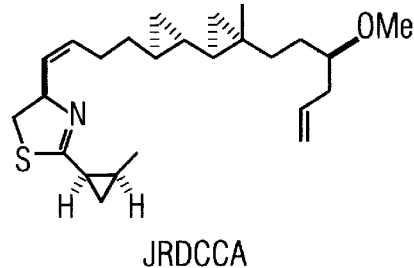
Figure 9:
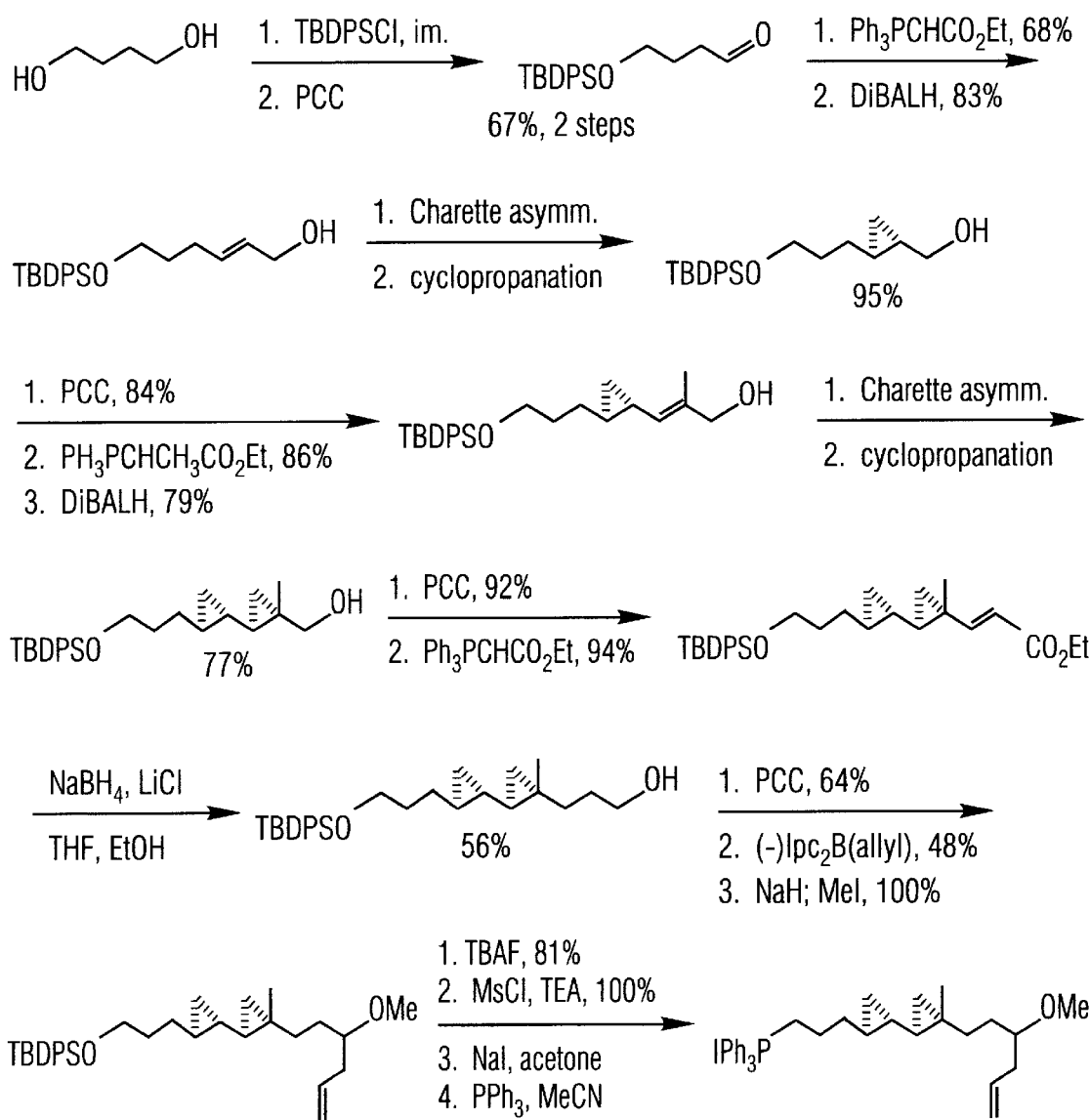
FIG. 9 shows a synthesis of diene-cyclopropanated curacin A.
Figure 10:
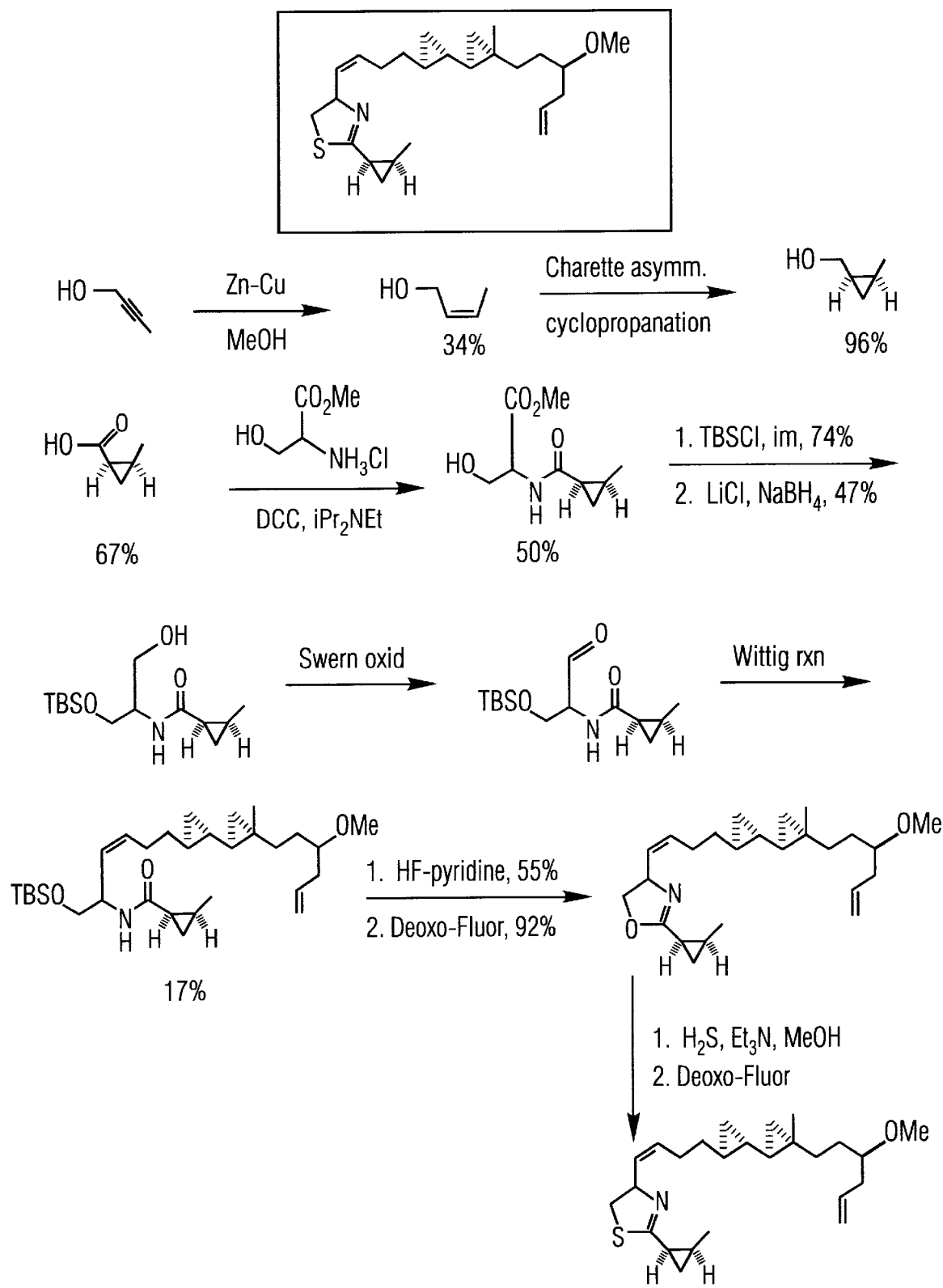
FIG. 10 demonstrates a synthesis of diene-cyclopropanated curacin A.
Figure 11:
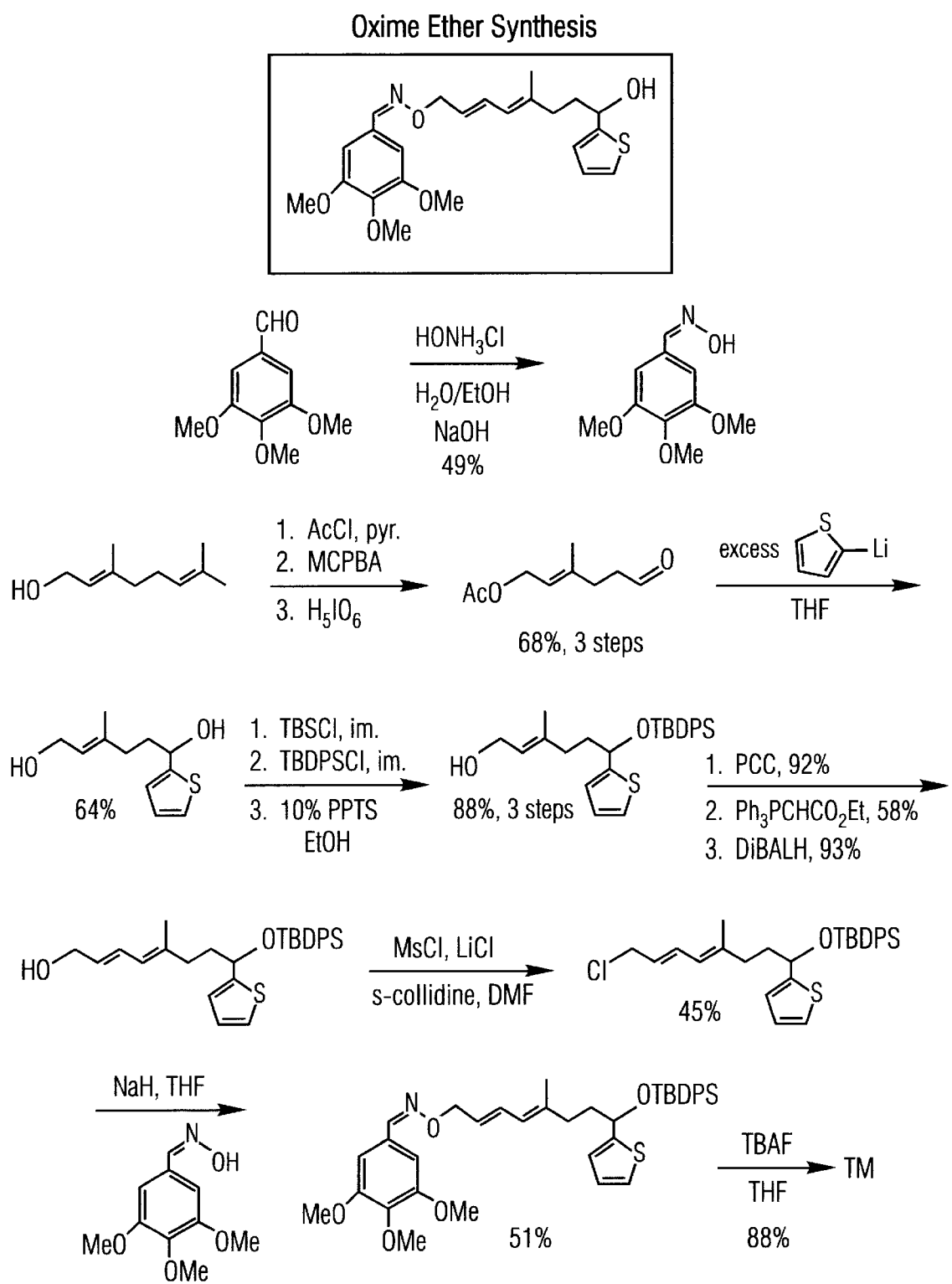
FIG. 11 depicts the synthesis of oxime ether.
Figure 12:
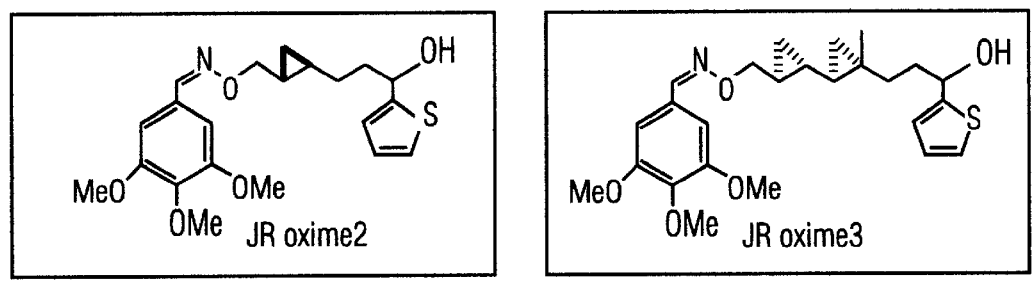
FIG. 12 illustrates the synthesis of additional oxime analogs.
Figure 12:
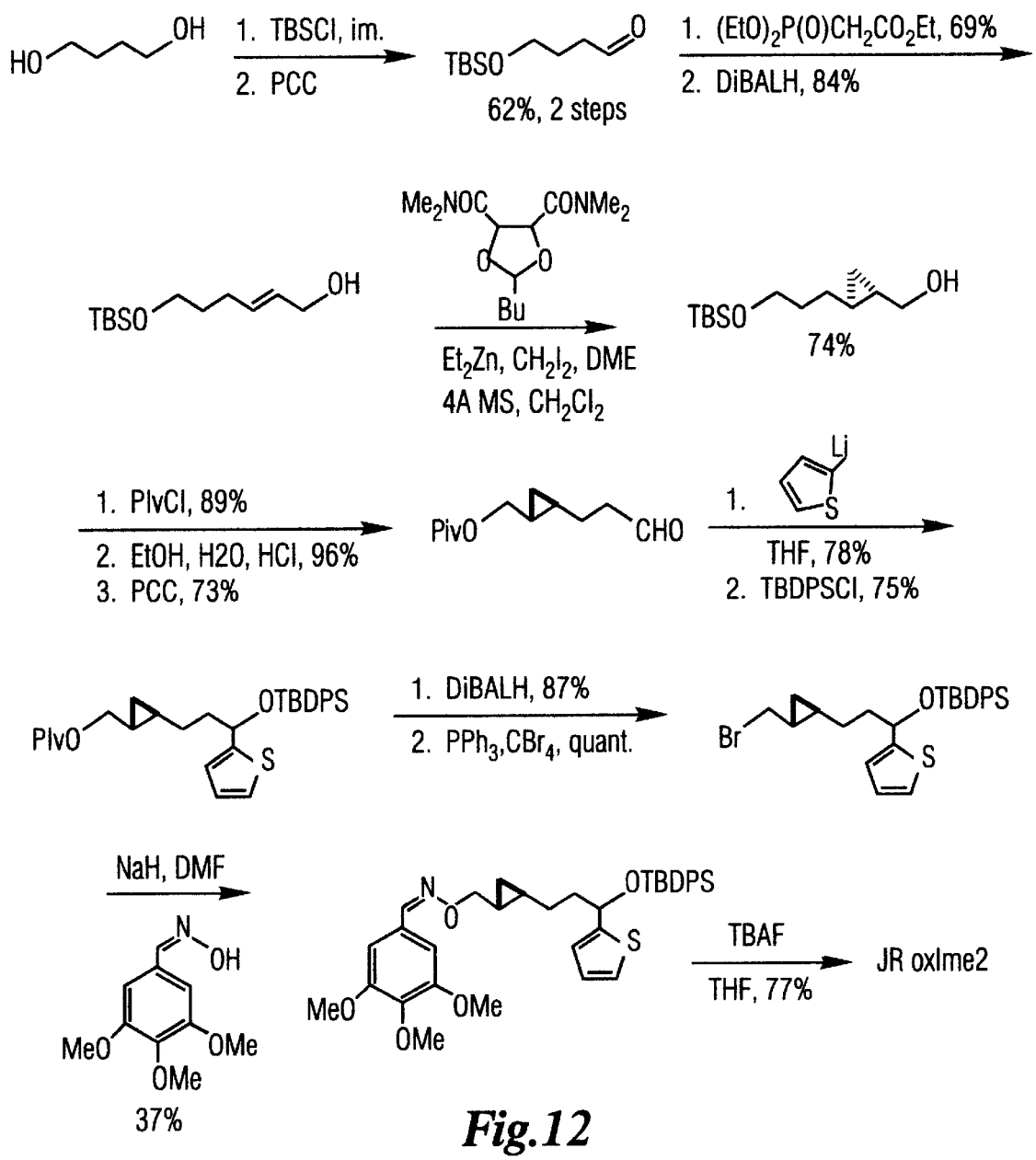
Figure 13A:
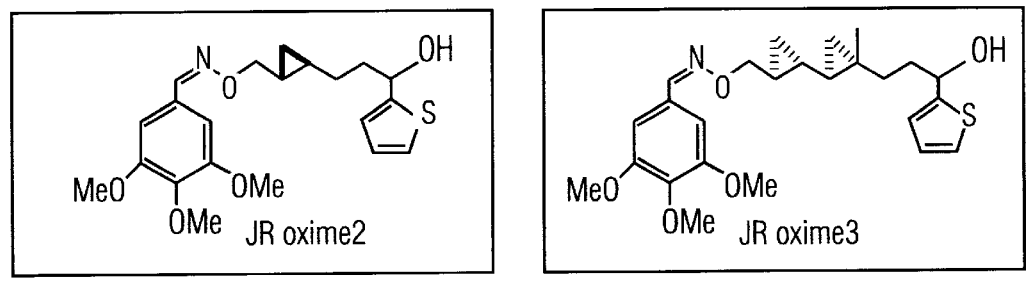
FIGS. 13a & b show the synthesis of additional oxime analogs.
Figure 13A:
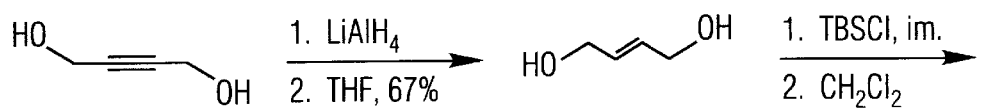
Figure 13A:
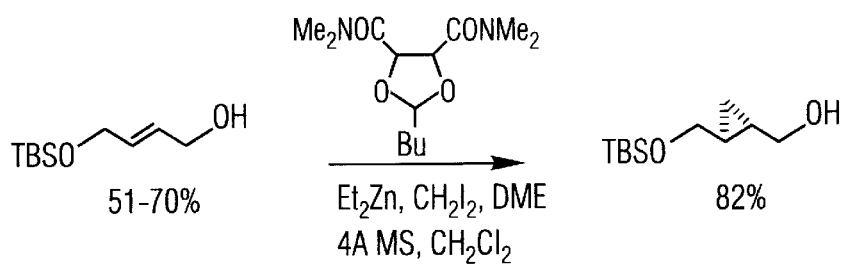
Figure 13A:
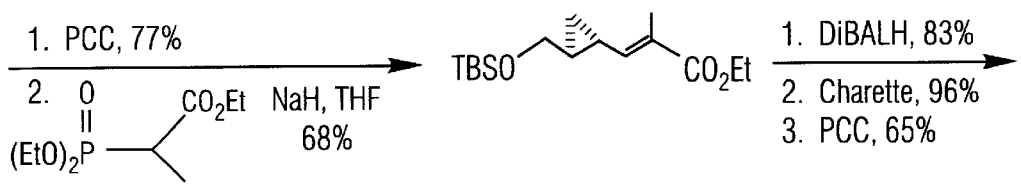
Figure 13A:
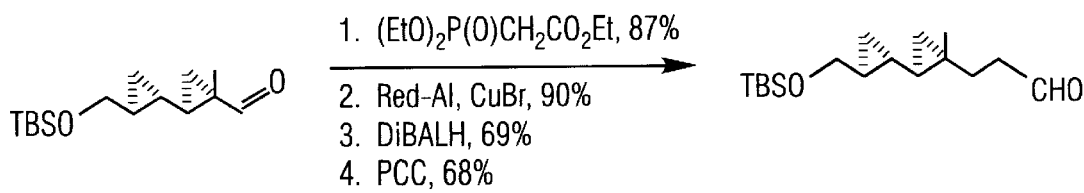
Figure 13A:
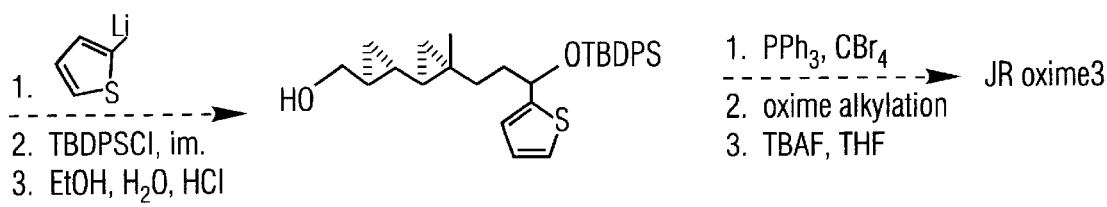
Figure 13B:
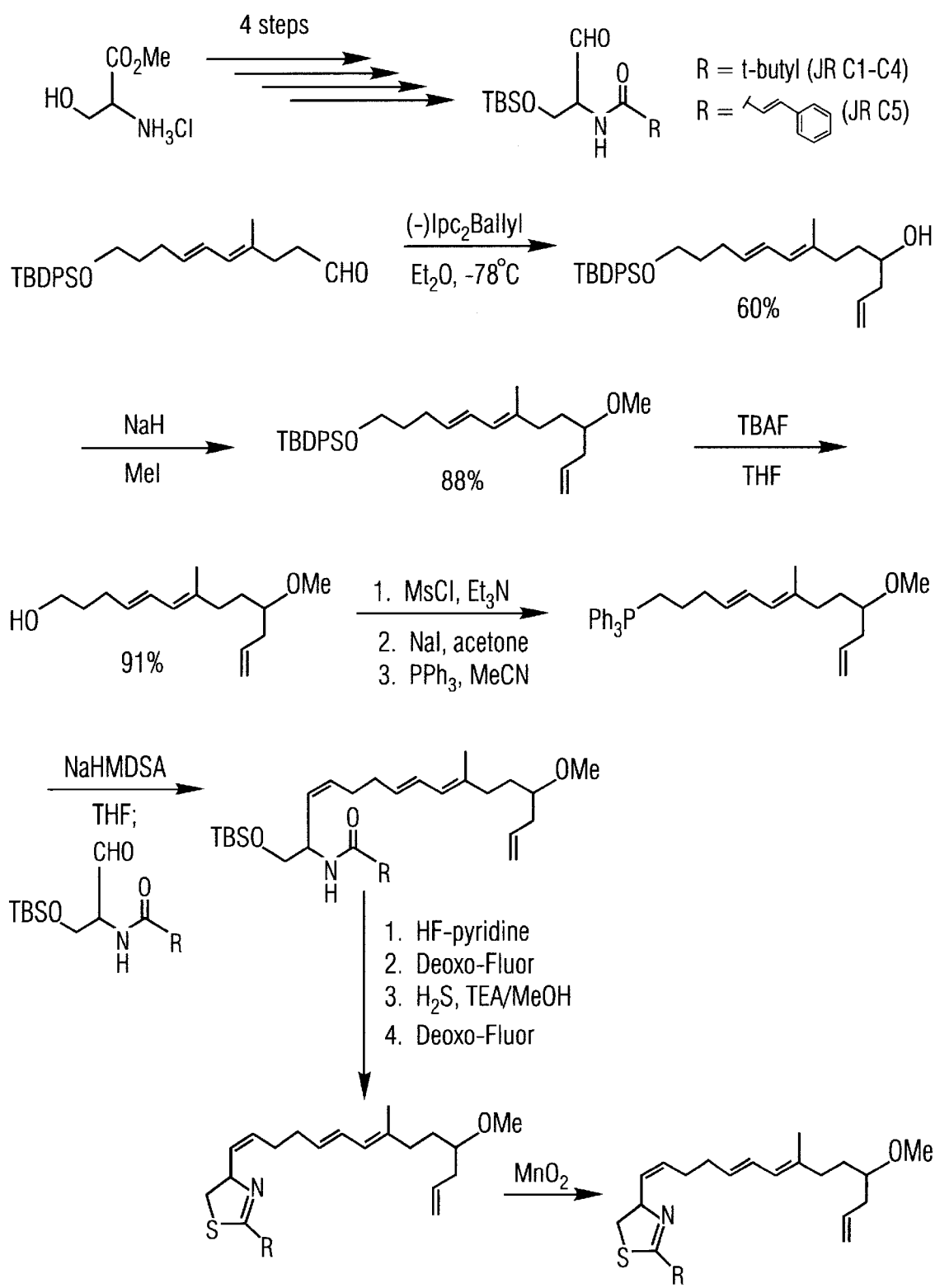
Figure 14:
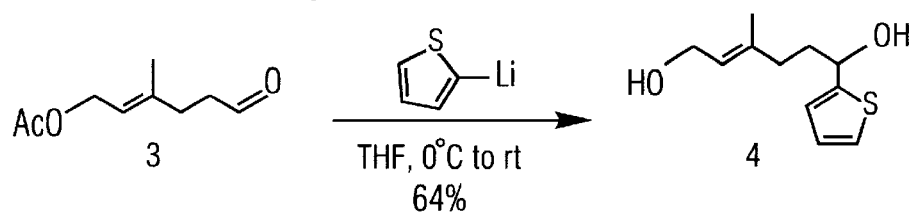
FIG. 14 depicts the synthesis of JRoxime1.
Figure 14:
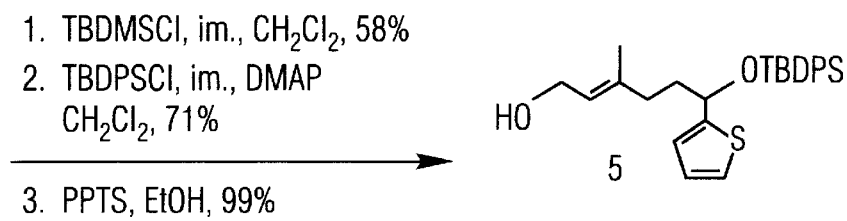
Figure 14:
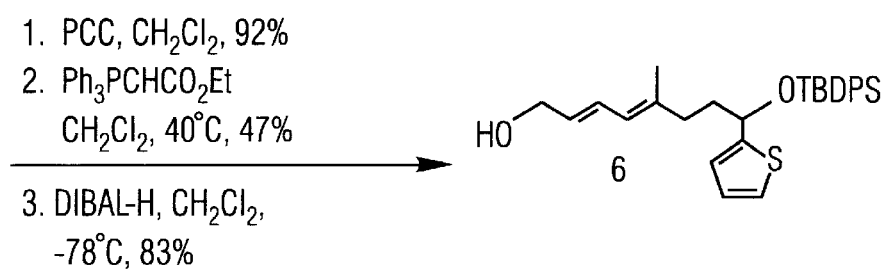
Figure 14:
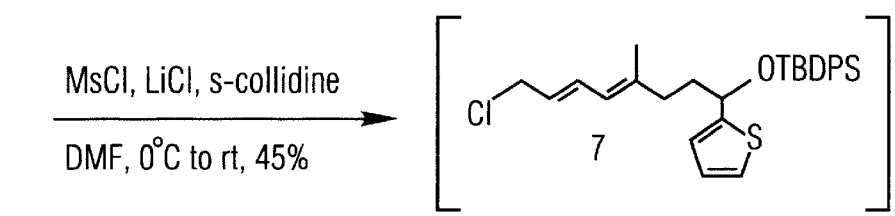
Figure 14:
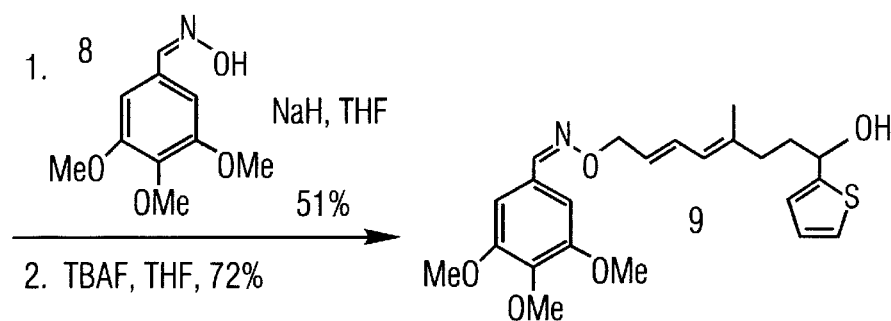

A particularly potent oxime analog of the antimitotic marine natural produce curacin A is identified in FIG. 8 as "JRoxime1." This much less lipophilic, structurally simplified derivative is only slightly weaker at inhibiting the growth of cultured human tumor cells than the natural product and found to be considerably more potent than curacin A at inhibiting the assembly of purified tubulin. FIG. 14 depicts the synthesis of JRoxime1. The inventors found that while 17c and 17e (FIG. 3) introduce effective replacements for the labile cyclopropyl thiazoline moiety and the homoallylic ether terminus of curacin A, they share the possibly undesirable (Z)-alkene moiety with the parent lead structure and are similarly highly lipophilic (clogP values of 5.3–6.6). Alkorta, I.; Villar, H. O., *Int. J. Quant. Chem.* 1992, 44, 203. In an effort to address both deficiencies, the inventors identified JRoxime1, which demonstrates superior bioactivity. The rational for replacing the (Z)-alkene moiety with an oxime stemmed from minimizing steric congestion at this position, retaining a π-system, and introducing a functional group that equilibrates between both cisoid- and transoid-geometries and lends itself to rapid modular analoging. For a preliminary proof-of-principle we selected peripheral substituents derived from the combinatorially optimized 17c. The synthesis of target molecule JRoxime1 was accomplished in ten steps, as shown in FIG. 14.

As shown in FIG. 14, treatment of aldehyde 3 with excess 2-thienyllithium and selective protection of the resulting diol 4 provided silyl ether 5. Corey, E. J.; Cane, D. E.; Libit, L., *J. Am. Chem. Soc.* 1971, 93, 7016. Oxidation of 5 to the α,β-unsaturated aldehyde with PCC and Wittig homologation followed by reduction of the dienyl ester with DIBAL-H led to dienyl alcohol 6. Corey, E. J.; Suggs, J. W. *Tetrahedron Lett.* 1975, 31, 2647. Mesylation and in situ allylic chloride formation gave the sensitive dienyl chloride 7, which was displaced without purification with the sodium salt of aldoxime 8 to give the oxime ether. Desilylation with TBAF in THF gave the desired oxime JRoxime1 9. Khadse, B. G.; Lokhande, S. R.; Bhamaria, R. P.; Prabhu, S. R. *Indian J. Chem. Sect. B* 1987, 26, 856.

Figure 15:
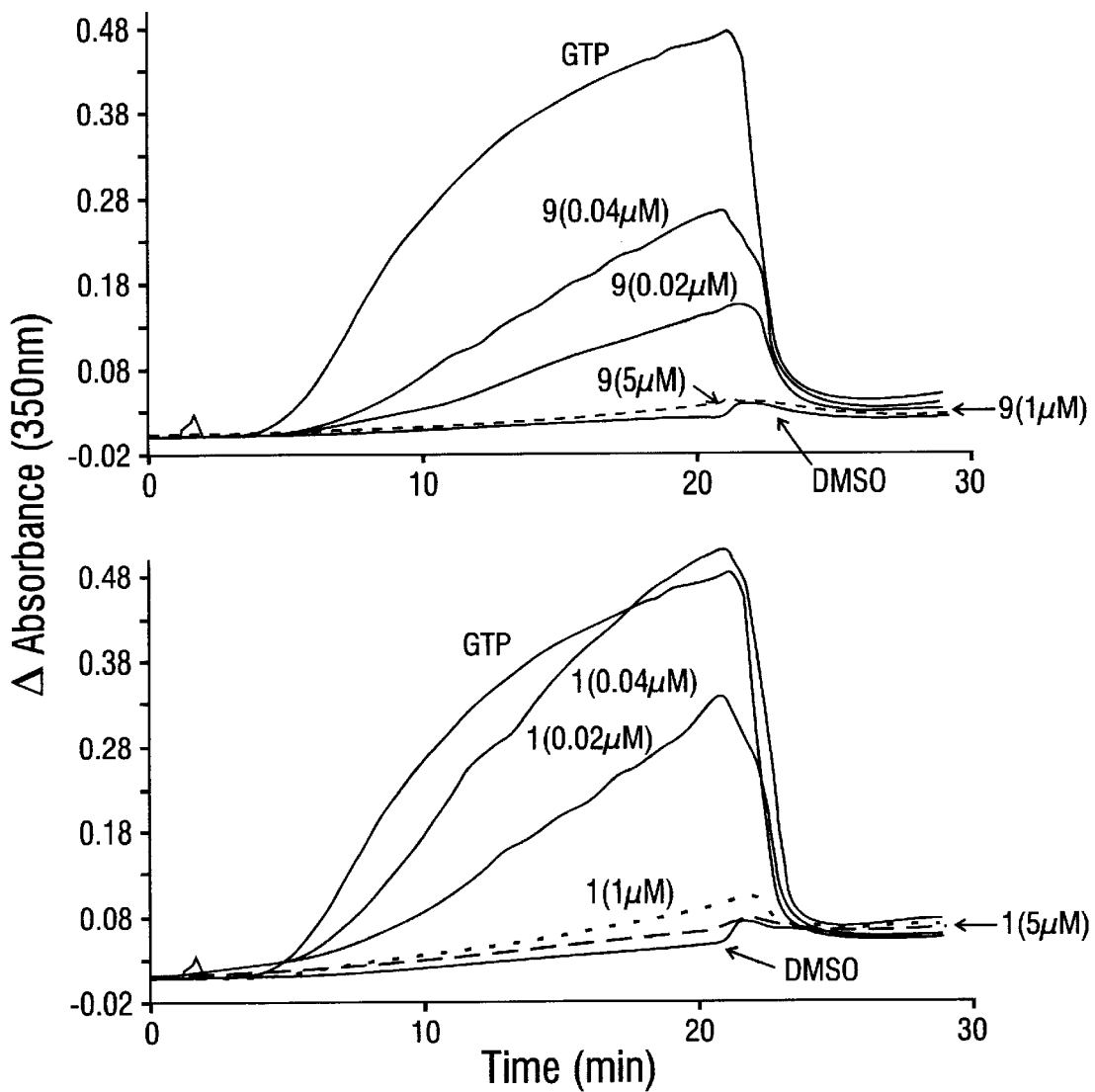
FIG. 15 illustrates plots that compare inhibition of GTP/glutamate-induced assembly of tubulin by 40 nM–1 $\mu$M concentrations of JRoxime1 and curacin A.

JRoxime1 was found to have potent antiproliferative activity in three human tumor cells lines: breast (MDA-MB231), prostate (PC3) and ovarian (2008). GI$_{50}$ values at 48 hours of continuous drug exposure were 0.12±0.10, 0.25±0.08 and 0.24±0.18 $\mu$M [means (N=4 over 10 concentrations)±SD], respectively. These values are, as those of our previously reported analogs 17c and 17e, highly comparable to those found for curacin A under identical conditions, namely 0.096±0.06, 0.050±0.009, 0.035±0.007 $\mu$M (N=7), respectively. Wipf, P; Reeves, J. T.; Balachandran, R.; Giuliano, K. A.; Hamel, E.; Day, B. W., *J. Am. Chem. Soc.* 2000, 122, 9391. Since curacin A binds with extremely high affinity at the colchicine site of tubulin, the inventors compared its ability with that of JRoxime1 to displace an equimolar (5 $\mu$M) concentration of pre-bound [$^3$H]colchicine from a 1:1 stoichiometric amount of isolated bovine brain tubulin at both 30° C. and 37° C. Verdier-Pinard, P.; Lai, J.-Y.; Yoo, H.-D.; Yu, J.; Marquez, B.; Nagle, D. G.; Nambu, M.; White, J. D.; Falck, J. R.; Gerwick, W. H.; Day, B. W.; Hamel, E. *Mol Pharmacol.* 1998, 53, 62. Wipf, P; Reeves, J. T.; Balachandran, R.; Giuliano, K. A.; Hamel, E.; Day, B. W., *J. Am. Chem. Soc.* 2000, 122, 9391. Curacin A displaced 78±2 and 87±9% (N=9) of the label at these respective temperatures, while Jroxime1 competed away 48±12 and 53±2%. The most impressive property of Jroxime1 was its ability to inhibit the GTP/glutamate-induced assembly of tubulin in a standard 30° C. turbidimetric assay, as shown in FIG. 15. Verdier-Pinard, P.; Lai, J.-Y.; Yoo, H.-D.; Yu, J.; Marquez, B.; Nagle, D. G.; Nambu, M.; White, J. D.; Falck, J. R.; Gerwick, W. H.; Day, B. W.; Hamel, E. *Mol. Pharmacol.* 1998, 53, 62. Wipf, P; Reeves, J. T.; Balachandran, R.; Giuliano, K. A.; Hamel, E.; Day, B. W., *J. Am. Chem. Soc.* 2000, 122, 9391. The activity of Jroxime1 in this assay was remarkable in that its IC$_{50}$ [0.17±0.09 $\mu$M (N=2 over 4 concentrations)] was far superior to that of curacin A [0.52±0.21 $\mu$M (N=2 over 4 concentrations)].

Further detailed explanations of the synthesis of some of the analog compounds and some of the intermediates follows. Additional explanatory information regarding the synthesis of these analogs can be found in FIGS. 2–13a and 13b. All moisture-sensitive reactions were performed under an atmosphere of $N_2$ and all glassware was dried in an oven at 140° C. prior to use. THF and Et$_2$ were dried by distillation over Na/benzophenone under a nitrogen atmosphere. Dry $CH_2Cl_2$ was obtained by distillation from $CaH_2$. Unless otherwise stated, solvents or reagents were used without further purification. Analytical thin layer chromatography (TLC) was performed on pre-coated silica gel 60 F-254 plates (particle size 0.040–0.055 mm, 230–400 mesh) and visualization was accomplished with a 254 nm UV light or by staining with a basic KMnO$_4$ solution or anisaldehyde dye. NMR spectra were recorded at 300 MHz/75 MHz ($^1$H/$^{13}$C NMR) in CDCl$_3$ unless stated otherwise. High and some low-resolution masses were determined by introduction with a direction insertion probe into a VG-70-70 HF spectrometer operating in the electron ionization (EI) mode.

Tert-Butyl-(4E,6E)-9-[1,3]dioxolan-2-yl-7-methyl-nona-4,6-dienyloxy)-diphenylsilane was synthesized in the following manner. A solution of aldehyde 3 (3.14 g, 7.48 mmol), ethylene glycol (0.90 mL, 15 mmol) and TsOH (15 mg, 0.078 mmol) in 28 mL of benzene was heated at 90° mL, 15 mmol) and TsOH (15 mg, 0.078 mmol) in 28 mL of benzene was heated at 90° C. for 2 hours in a Dean-Stark apparatus. The reaction mixture was cooled, quenched with a saturated NaHCO$_3$ solution, extracted with Et$_2$O, dried Na$_2$SO$_4$), and concentrated to give 3.40 g (7.39 mmol, 99%) of oily tert-butyl-(4E,6E)-(9-[1,3]dioxolan-2-yl-7-methyl-nona-4,6-dienyloxy)-diphenylsilane which was used without further purification: $^1$H NMR 67 7.70–7.66 (m, 4H), 7.43–7.36 (m, 6H), 6.26 (dd, 1H, J=14.9, 10.9 Hz), 5.84 (d, 1H, J=10.7 Hz), 5.57 (dt, 1H, J=14.4, 7.0 Hz), 4.88 (t, 1H, J=4.8 Hz), 4.00–3.75 (m, 4H), 3.69 (t, 2H, J=6.4 Hz), 2.24–2.15 (m,4H), 1.85–1.60 (m, 4H), 1.70 (s, 3H), 1.07 (s, 9H).

(4E,6E)-9-[1,3]Dioxolan-2-yl-7-methyl-nona-4,6-dien-1-ol was synthesized in the following manner. A solution of tert-butyl-(4E,6E)-(9-[1,3]dioxolan-2-yl-7-methyl-nona-4,6-dienyloxy)-diphenyl-silane (3.35 g, 7.28 mmol) in 75 mL of THF was cooled to 0° C. and treated dropwise with 10 mL of a 1 M solution of TBAF in THF. The reaction mixture was stirred at 0° C. to room temperature for 11 hours, quenched with a saturated NaHCO$_3$ solution, extracted with Et$_2$O, dried (Na$_2$SO$_4$), and concentrated. Purification of the residue by column chromatography on SiO$_2$ (2:1 hexanes-EtOAc) provided 1.44 g (6.38 mmol, 88%) of oily (4E,6E)-9-[1,3]dioxolan-2-yl-7-methyl-nona-4,6-dien-1-ol: $^1$H NMR δ6.28 (dd, 1H, J=14.9, 10.9 Hz), 5.84 (d, 1H, J=10.7 Hz), 5.59 (dt, 1H, J=14.4, 7.0 Hz), 4.86 (t, 1H, J=4.7 Hz), 4.00–3.80 (m, 4H), 3.67 (t, 2H, J=6.5Hz) 2.50–2.38 (m, 1H), 2.25–2.10 (m, 4H), 1.80–1.75 (m, 2H), 1.75 (s, 3H), 1.68 (p, 2H, J=6.7 Hz).

Methanesulfonic acid (4E,6E)-9-[1,3]dioxolan-2-yl-7-methyl-nona-4,6-dienyl ester was synthesized using the following procedure. To a cooled (0° C.) solution of (4E,6E)-9-[1,3]dioxolan-2-yl-7-methyl-nona-4,6-dien-1-ol (1.60 g, 7.20 mmol), triethylamine (1.2 mL, 8.6 mmol), and 15 mL of CH$_2$Cl$_2$ was added dropwise methanesulfonyl chloride (0.61 mL, 7.9 mmol). The reaction mixture was stirred at 0° C. to room temperature for 2.5 h, quenched with a saturated NaHCO$_3$ solution, extracted with EtOAc, dried (Na$_2$SO$_4$), and concentrated to give 1.95 g (6.41 mmol, 89%) of methanesulfonic acid (4E,6E)-9-[1,3]dioxolan-2-yl-7-methyl-nona-4,6-dienyl ester which was used without further purification: $^1$H NMR δ6.28 (dd, 1H, J-15.0, 10.9 Hz), 5.82 (d, 1H,J-10.7 Hz), 5.52 (dt, 1H,J-15.0, 7.0 Hz), 4.85 (t, 1H,J-4.8 Hz), 4.23 (t, 2H, J-6.4 Hz), 4.00–3.75 (m, 4H), 3.00 (s, 3H), 2.25–2.12 (m, 4H), 1.90–1.75 (m, 4H), 1.74 (s, 3H).

For the synthesis of (3E-5E)-2-(9-Iodo-3-methyl-nona-3,5-dienyl)-[1,3]dioxolane (4), a mixture of methanesulfonic acid (4E,6E)-9-[1,3]dioxolan-2-yl-7-methyl-nona-4,6-dienyl ester (1.95 g, 6.41 mmol), NaI (3.31 g, 22.1 mmol), and 45 mL of acetone was heated at reflux for 2 hours, cooled, and concentrated. The crude residue was filtered through a pad of SiO$_2$ (pentane/Et$_2$O, 4:1). Concentration of the filtrate gave 1.60 g (4.76 mmol, 74%) of oily 4 which was used without further purification: $^1$H NMR δ6.30 (dd, 1H. J-14.9, 10.8 Hz), 5.83 (d, 1H,J-10.7 Hz), 5.51 (dt, 1H, J=14.5, 7.1 Hz), 4.87 (t, 1H, J=4.7 Hz), 4.00–3.80 (m, 4H), 3.20 (t, 2H, J=6.9 Hz), 2.26–2.14 (m, 4H), 1.92 (p, 2H, J-7.1 Hz), 1.85–1.75 (m, 2H), 1.76 (s, 3H).

For the synthesis of (4E,6E)-(9-[1,3]dioxolan-2-yl-7-methyl-nona-4,6-dienyl)triphenylphosphonium iodide, after bubbling N$_2$ through a solution of iodide 4 (1.60 g., 4.76 mmol) in 30 mL of MeCN for 10 minutes, PPh$_3$ (2.49 g, 9.50 mmol) was added, and the reaction mixture was heated at reflux for 11 hours, cooled, and concentrated. The residue was rinsed with pentane to remove excess PPh$_3$, and dried in vacuo to give 2.85 g (4.76 mmol, quant.) of (4E,6E)-(9-[1,3]dioxolan-2-yl-7-methyl-nona-4,6-dienyl) triphenylphosphorium iodide as a wax.

2-[(3E,5E,9Z)-10-(2,4-Dimethoxyphenyl)-3-methyl-deca-3,5,9-trienyl]-[1,3]dioxolane was made in the following manner. To a −78° C. solution of (4E,6E)-(9-[1,3]dioxolan-2-yl-7-methyl-nona-4,6-dienyl) triphenylphosphonium iodide (910 mg, 1.52 mmol) in 8 mL of THF was added dropwise 0.83 mL of a 2 M solution of NaHMDS in THF. After 40 minutes at −78° C., a solution of 2,4-dimethoxybenzaldehyde (303 mg, 1.84 mmol) in 3 mL of THF was added dropwise. The reaction was warmed to 0° C. over 2 hours, brine was added, and the mixture was extracted with Et$_2$O. The combined organic extracts were washed with a saturated solution of NaHCO$_3$, dried (Na$_2$SO$_4$) and concentrated. Chromatography on SiO$_2$ (hexanes/EtOAc, 10:1) gave 337 mg (0.941 mmol, 62%) of oily 2-[(3E,5E,9Z)-10-(2,4-dimethoxyphenyl)-3-methyl-deca-3,5,9-trienyl]-[1,3]dioxolane as a 5:1 mixture of (9Z):(9E)isomers: $^1$H NMR δ7.16–7.13 (m, 1H), 6.50–6.40 (m, 3H), 6.25 (dd, 1H, J=14.9, 10.9 Hz), 5.82 (d, 1H, J=10.5 Hz), 5.70–5.50 (m, 2H), 4.85 (t, 1H, J=4.7 Hz), 3.97–3.84 (m, 4H), 3.81 (s, 6H), 2.36–2.31 (m, 2H), 2.30–2.10 (m, 4H), 1.81–1.74 (m, 2H), 1.73 (s, 3H).

2-[(3E,5E,9Z)-10-(2,5-Dimethoxyphenyl)-3-methyl-deca-3,5,9-trienyl]-[1,3]dioxolane was synthesized as follows: to a −78° C. solution of (4E,6E)-(9-[1,3]dioxolan-2-yl-7-methyl-nona-4,6-dienyl)triphenylphosphonium iodide (500 mg, 0.840 mmol) in 5 mL of THF was added dropwise 0.5 mL of a 2 M solution of NaHMDS in THF. After 40 minutes at −78° C., a solution of 2,5-dimethoxybenzaldehyde (167 mg, 1.01 mmol) in 1 mL of THF was added dropwise. The reaction was warmed to 0° C. over 2 hours, brine was added, and the mixture was extracted with Et$_2$O. The combined organic extracts were washed with a saturated solution of NaHCO$_3$, dried (Na$_2$SO$_4$) and concentrated. Chromatography on SiO$_2$ (hexanes/EtOAc 10:1) gave 162 mg (0.453 mmol, 54%) of oily 2-[(3E,5E,9Z)-10-(2,5-dimethoxphenyl))-3-methyl-deca-3,5,9-trienyl]-[1,3] dioxolane as a 5:1 mixture of (9Z):(9E) isomers: $^1$H NMR δ6.82–6.70 (m, 3H), 6.51 (d, 1H, J=11.5 Hz), 6.25 (dd, 1H, J=15.2, 11.0 Hz), 5.82 (d, 1H, J=10.6 Hz), 5.78–5.69 (m, 1H), 5.60 (dt, 1H, J=14.1, 6.8 Hz), 4.85 (t, 1H, 4.7 Hz), 3.97–3.82 (m, 4H), 3.78 (s, 3H), 3.76 (s, 3H), 2.39–2.31 (m, 2H), 2.30–2.21 (m, 2H), 2.20–2.10 (m, 2H). 181–1.72 (m, 2H), 1.73 (s, 3H).

For the preparation of 2-[(3E,5E,9Z)-10-(3,4,5-Trimethoxyphenyl)-3-methyl-deca-3,5,9-trien-yl]-[1,3] dioxolane, to a −78° C. solution of (4E,6E)-(9-[1,3] dioxolan-2yl-7-methyl-nona-4,6-dienyl) triphenylphosphonium iodide (500 mg, 0.840 mmol) in 5 mL of THF was added dropwise 0.5 mL of 2 M solution of NaHMDS in THF. After 1 hour at −78° C., a solution of 3,4,5-trimethoxybenzaldehyde (197 mg, 1.01 mmol) in 1 mL of THF was added dropwise. The reaction was warmed to 0° C. over 2.5 hours, brine was added, and the mixture was extracted with Et$_2$O. The combined organic extracts were washed with a saturated solution of NaHCO$_3$, dried (Na$_2$SO$_4$) and concentrated. Chromatography on SiO$_2$ (hexanes/EtOAC, 4:1) gave 178 mg (0.459 mmol, 55%) of oily 2-[(3E,5E,9Z)-10-(3,4,5-trimethoxyphenyl)-3-methyl-deca-3,5,9-trienyl]-[1,3]dioxolane as 4:1 mixture of (9Z):(9E) isomers: 1H NMR δ6.49 (s, 2H), 6.36 (d, 1H, J=11.5 Hz), 6.26 (dd, 1H, J=14.9, 10.6 Hz), 5.82 (d, 1H, J-10.7 Hz), 5.66–5.55 (m, 2H), 4.83 (t, 1H, J=4.7 Hz), 3.96–3.92 (m, 2H), 3.90–3.76 (m, 11H), 2.46–2.41 (m, 2H), 2.30–2.22 (m, 2H), 2.17–2.10 (m, 2H), 1.80–1.73 (m, 2H), 1.71 (s, 3H).

For the synthesis of (4E,6E,10Z)-11-(2,4-Dimethoxyphenyl)-4-methyl-undeca-4,6,10-trienal (5), a solution of 2-[(3E,5E,9Z)-10-(2,4-dimethoxyphenyl)-3-methyl-deca-3,5,9-trienyl][1,3]dioxolane (233 mg, 0.651 mmol) in 20 mL of acetone/$H_2O$ (5:1) was treated with TsOH (110 mg, 0.579 mmol), heated at 70° C. for 3 hours, quenched with a saturated $NaHCO_3$ solution, extracted with $Et_2O$ (5×), dried ($Na_2SO_4$) and concentrated. Purification of the residue by chromatography on $SiO_2$ (hexanes/EtOAc, 9:1) gave 132 mg (0.618 mmol, 95%) of oily 5: $^1$H NMR δ9.78 (s, 1H), 7.16 (d, 1H, J=8.9 Hz), 6.50–6.45 (m, 3H), 6.24 (dd, 1H, J=14.9, 10.8 Hz), 5.80 (d, 1H, J=10.6 Hz), 5.70–5.61 (m, 2 H) 3.92–3.82 (m, 9H), 2.59–2.54 (m, 2H), 2.44–2.33 (m, 4H), 2.30–2.20 (m, 2H), 1.74 (s, 3 H); MS (EI) m/z (rel. intensity) 314 (M$^+$, 1), 177 (100); HRMS (EI) calculated for $C_{20}H_{26}O_3$: 314.1882, found 314.1888.

For the synthesis of (4E,6E,10Z)-11-(2,5-Dimethoxyphenyl)-4-methyl-undeca-4,6,10-trienal (6), a solution of 2-[(3E,5E,9Z)-10-(2,5-dimethoxyphenyl)-3-methyl-deca-3,5,9-trienyl]-[1,3]dioxolane (162 mg, 0.452 mmol) in 10 mL of acetone/$H_2O$ (5:1treated with TsOH (100 mg, 0.520 mmol), heated at 70° C for 3 hours, quenched with a saturated $NaHCO_3$ solution, extracted with $Et_2O$ (5×), dried ($Na_2SO_4$) and concentrated. Purification of the residue by chromatography on $SiO_2$ (hexanes/EtOAc, 9: 1) gave 145 mg (0.420 mmol, 93%) of oily δ6: $^1$H NMR δ9.77 (t, 1H, J=1.5 Hz), 6.84–6.70 (m, 3H), 6.51 (d, 1H, J=11.6 Hz), 6.23 (dd, 1H, J=14.8, 11.0 Hz), 5.84–5.56 (m, 3H), 3.79 (s, H); MS (EI) m/z (rel. intensity) 314 (M$^+$, 9), 177 (100); HRMS (EI) calculated for $C_{20}H_{26}O_3$: 314.1882, found: 314.1880.

To synthesize (4E,6E, 10Z)-11-(3,4,5-Trimethoxyphenyl)-4-methyl-undeca-4,6,10-trienal (7), a solution of 2-[(3E,5E,9Z)-10-(3,4,5-trimethoxyphenyl)-3-methyl-deca-3,5,9-trienyl][1,3]dioxolane (178 mg, 0.459 mmol) in 10 mL of acetone/$H_2O$ (5:1) was treated with TsOH (100 mg, 0.520 mmol), heated at 70° C. for 3 hours, quenched with a saturated $NaHCO_3$ solution, extracted with $Et_2O$ (5×), dried ($Na_2SO_4$) and concentrated. Purification of the residue by chromatography on $SiO_2$ (hexanes/EtOAc, 9:1) gave 145 mg (0.422 mmol, 92%) of oily 7:$^1$H NMR δ9.74 (t, 1H, J=1.4 Hz), 6.49 (s, 2H), 6.36 (d, 1 H, J=11.5 Hz), 6.30–6.20 (m, 1H), 5.79 (d, 1H, J=10.6 Hz), 5.66–5.57 (m, 2H), 3.83(s, 9H), 2.56–2.51 (m, 2H), 2.49–2.41 (m, 2H), 2.37–2.32 (m, 2H), 2.27–2.22 (m, 2H), 1.71 (s, 3H): MS (EI) m/z (rel. intensity) 344 (M$^{30}$, 15), 319 (7), 290 (10), 207 (100), 176 (60); HRMS (EI) calculated for $C_{21}H_{28}O_4$: 344.1988, found: 344;1999.

The 15mix was synthesized in the following manner: to a premixed 0.5M solution of equimolar amounts of furan (freshly distilled), thiophene, benzofuran (freshly distilled), benzothiophene, anisole, and 1,4-dimethoxybenzene in THF (156 μL, 0.0780 mmol total) in 0.5 mL of THF at −78° C. was added dropwise to 46 μL (0.078 mmol) of a solution of 1.7 M t-BuLi in pentane. The reaction mixture was stirred for 1 hour, allowed to warm from −78° to 0° C., and recooled to −78° C. A solution of aldehyde 5 (8.2 mg, 26 μmol) in 0.4 mL of THF was added dropwise. The reaction mixture was allowed to warm to room temperature over 3 hours, quenched with saturated $NaHCO_3$ solution and extracted with $Et_2O$. The combined organic extracts were washed with brine, dried ($Na_2SO_4$), and concentrated. The crude product mixture was dissolved in 10 mL of THF. Vinyl ether 11 (621 mg, 653 μmol) was added, followed by camphorsulfonic acid (12 mg, 52 μmol). The reaction mixture was heated to reflux for 70 minutes, cooled to room temperature, quenched with saturated $NaHCO_3$ solution, and concentrated to remove THF. MeCN was added and the organic/aqueous mixture was extracted four times with FC-72. The combined FC-72 extracts were dried ($Na_2SO_4$) and concentrated to give 637 mg of colorless solid 12mix that was dissolved in 5 mL of $Et_2O$ and 3 mL of MeOH. After addition of camphorsulfonic acid (15.2 mg, 66.0 μmol), the reaction mixture was stirred at room temperature for 3 hours. Saturated $NaHCO_3$ solution was added, and the mixture was concentrated. MeCN was added, and the organic/aqueous mixture was extracted four times with FC-72. The organic and FC-72 phases were dried ($Na_2SO_4$) and concentrated. The organic phase yielded 8.1 mg of a light yellow oily 15mix, while the fluorous has yielded 503 mg (544 μmol) of hydrolysis product of 11.

16mix was synthesized according to the procedure used for 15mix, 6 (9.1 mg, 29 μmol) and 11 (551 mg, 580 μmol) provided 8.8 mg of 16mix as a yellow oil and 462 mg (500 μmol) of hydrolysis product of 11.

17mix was synthesized according to the procedure used for 15mix, 7 (10.2 mg, 30 μmol) and 11 (560 mg, 589 μmol) provided 8.8 mg of 17mix as a yellow oil and 462 mg (500 μmol) of hydrolysis product of 11.

For the preparation of (4E,1E,10Z)-11-(3,4,5-Trimethoxyphenyl)-4-methyl-1-furan-2-ylundeca-4,6,10-trien-1-ol (17a), a solution of 7 (4.9 mg, 14 μmol) in 1.0 mL of THF was added dropwise at −78° C. to 1 mL (0.2 mmol) of an approximately 0.2 M solution of lithiated furan in THF. The reaction mixture was allowed to warm to 0° C. over 1 hour, quenched with a saturated $NaHCO_3$ solution, extracted with $Et_2O$, dried ($Na_2SO$), and concentrated. Purification of the residue by chromatography on $SiO_2$ (hexanes/EtOAc, 9:1) provided 4.9 mg (12 μmol, 84%) of 17a as an oil: IR (neat) 3450, 3006, 2927, 1584, 1509, 1236, 1125 cm$^{-1}$; $^1$H NMR δ7.38 (s, 1H), 6.50 (s, 2H), 6.38 (d, 1H, J=11.5 Hz), 6.33–6.31 (m, 1H), 6.29–6.24 (m, 1H), 6.23 (d, 1H, J=2.1 Hz), 5.83 (d, 1H, J=10.6 Hz), 5.69–5.56 (m, 2H), 4.68–4.64 (m, 1H), 3.85 (s, 9H), 2.48–2.42 (m, 2H), 2.30–1.90 (m, 6H), 1.74 (s, 3H); $^{13}$C NMR δ142.0, 131.8, 131.6, 129.3, 127.2, 125.1, 110.2, 105.8, 102.9, 67.4, 61.0, 56.1, 35.6, 33.6, 33.2, 29.7, 28.7, 27.3, 16.5; MS (EI) m/z (rel. intensity) 412 (M$^+$, 7), 207 (100), 176 (45); HRMS (EI) calculated for $C_{25}H_{32}O_5$: 412.2250, found: 412.2234.

(4E,6E,10Z)-11-(3,4,5-Trimethoxyphenyl)-4-methyl-1-benzothiophen-2ylundeca-4,6,10-trien-1ol (17b) was prepared according to the procedure used for 17a, but using lithiated benzothiophene 7 (6.7 mg, 19 μmol) provided 7.9 mg (17 μmol, 85%) of oily 17b: IR (neat) 3461, 3002, 2923, 1580, 1509, 1236, 1125 cm$^{-1}$; $^1$H NMR δ7.81 (d, 1H, J=8.4 Hz), 7.71 (d, 1H, J=6.8 Hz), 7.37–7.26 (m, 2H), 7.19 (s, 1H), 6.50 (s, 2H), 6.37 (d, 1H, J=11.5 Hz), 6.27 (dd, 1H, J=12.5, 8.2 Hz), 5.84 (d, 1H, J=10.7 Hz), 5.68–5.55 (m, 2H), 5.00–4.90 (m, 1H), 3.85 (s, 9H), 2.48–2.42 (m, 2H), 2.30–1.95 (m, 6H), 1.75 (s, 3H); $^{13}$C NMR δ131.8, 131.7, 129.3, 127.1, 125.3, 124.3, 124.2, 123.5, 122.5, 120.3, 105.8, 102.9, 70.6, 61.0, 56.1, 37.0, 35.8, 33.1, 32.8, 29.7, 28.7, 16.6; MS (EI) m/z (rel. intensity) 478 (M$^+$, 1), 207 (100), 176 (37); HRMS (EI) calculated for $C_{29}H_{34}O_4S$: 478.2178, found: 478.2160.

(4E,6E,10Z)-11-(3,4,5-Trimethoxyphenyl)-4-methyl-1-thiophen-2-ylundeca-4,6,10-trien-1-ol (17c) was prepared according to the procedure used for 17a, but using litiated thiophene 7 (5.2 mg, 15 μmol) provided 5.2 mg (12 μmol, 81%) of oily 17c: IR (neat) 3465, 3002, 2927, 1580, 1505, 1236, 1125 cm$^{-1}$; $^1$H NMR δ7.26 (s, 1H), 6.98–6.96 (m, 2H), 6.50 (s, 2H), 6.38 (d, 1H, J=11.5 Hz), 6.27 (dd, 1H, J=13.0, 8.9 Hz 5.83 (d, 1H, J=10.8 Hz), 5.70–5.55 (m, 2H), 4.92–4.82 (m, 1H), 3.85 (s, 9H), 2.48–2.42 (m, 2H), 2.31–2.21 (m, 2H), 2.20–2.08 (m, 2H), 2.06–1.90 (m, 2H), 1.74 (s, 3H); $^{13}$C NMR δ131.8, 131.7, 129.3, 127.2, 126.7, 125.2, 124.7, 123.8, 105.9, 103.0,70.0, 61.0, 56.1, 37.3, 36.0, 33.2, 32.8, 28.7, 25.1, 16.6; MS (EI) m/z (rel. intensity) 428 (M$^+$, 7), 207 (100), 176 (45), 91 (55); HRMS (EI) calculated for $C_{25}H_{32}O_4S$: 428.2021, found: 428.2012.

(4E,6E,10Z)-11-(3,4,5-Trimethoxyphenyl)-4-methyl-1-(2-methoxy-phenyl)-2-ylundeca-4,6,10-trien-1-ol (17d) was prepared according to the procedure used for 17a, but using litiated anisole 7 (5.5 mg, 16 μmol) provided 5.8 mg (13 μmol, 80%) of oily 17d: IR (neat) 3473, 3002, 2923, 1580, 1509, 1240, 1125 cm$^{-1}$; $^1$H NMR δ7.31–7.20 (m, 2 H), 6.95 (t, 1H, J=7.3 Hz), 6.88 (d, 1H, J-8.2 Hz), 6.50 (s, 2H), 6.37 (d, 1H, J=11.6 Hz), 6.36–6.20 (m, 1H), 5.84 (d, 1H, J=10.6 Hz), 5.67–5.60 (m, 2H), 4.83 (q,1H, J=6.3 Hz), 3.85 (s. 9H), 2.55–2.42 (m, 2H), 2.30–2.21 (m, 2H), 2.20–2.04 (m, 2H), 1.95–1.80 (m, 2H), 1.73 (s, 3H); $^{13}$ C NMR δ131.9, 131.3, 131.2, 130.1, 129.9, 129.3, 128.3, 127.4, 127.3, 124.7, 120.8, 110.5, 105.9, 103.0, 70.9, 61.0,56.1, 55.3, 36.3, 35.4, 33.2, 28.8, 16.6; MS (EI) m/z (rel. intensity) 452 (M$^+$, 2), 207 (100), 176 (47), 91 (88); HRMS (EI) calculated for $C_{28}H_{36}O_5$: 452.2563, found: 452.2547.

(4E,6E,10Z)-11-(3,4,5-Trimethoxyphenyl)-4-methyl-1-benzofuran-2-ylundeca-4,6,10-trien-1-ol (17e) was prepared according to the procedure used for 17a, but using lithiated benzofuran 7 (6.0 mg, 17 μmol) provided 6.4 mg (14 μmol, 79%) of oily 17e: IR (neat) 3442, 2923, 2851, 1576, 1509, 1236, 1133 cm$^{-1}$; $^1$H NMR δ7.54 (d, 1H), J=7.4 Hz), 7.45 (d, 1H, J=7.8 Hz), 7.30–7.15 (m, 2H), 6.62 (s, 1H), 6.50 (s, 2H), 6.37 (d, 1H, J=11.5 Hz), 6.28 (dd, 1H, J=13.3, 9.1 Hz), 5.90–5.80 (m, 1H), 5.70–5.55 (m, 2H), 4.85–4.75 (m,1H), 2.46 (q, 2H, J=7.2 Hz), 2.32–2.00 (m, 6H), 1.75 (s, 3H); $^{13}$C NMR δ135.8, 131.8, 130.1, 129.8, 129.3, 127.1, 125.3, 124.2, 122.8, 121.1, 111.3, 105.8, 102.9, 102.7, 67.9, 61.0, 56.1, 35.5, 33.6, 33.2, 28.7 16.6; MS (EI) m/z (rel. intensity) 462 (M$^+$, 8), 207 (100), 176 (35); HRMS (EI) calculated for $C_{29}H_{34}O_5$; 462.2406, found: 462.2406.

(4E,6E,10Z)-11-(3,4,5-Trimethoxyphenyl)-4-methyl-1-(2,5-dimethoxy-phenyl)-2-ylundeca-4,6,10-trien-1-ol (17f) was prepared according to the procedure used for 17a, but using lithiated, 1,4-dimethoxybenzene 7 (7.1 mg, 21 μmol) provided 7.8 mg (16 μmol, 78%) of oily 17f: IR (neat) 3505, 2998, 2935, 2836, 1580, 1501, 1240, 1129 cm$^{-1}$; $^1$H NMR δ6.90–6.86 (m, 1H), 6.81–6.72 (m, 2H), 6.50 (s, 2H), 6.37 (d, 1H, J=11.6 Hz), 6.33–6.24 (m, 1H), 5.84 (d, 1H, J=10.7 Hz), 5.68–5.55 (m, 2H), 4.80 (t, 1H, J=5.8 Hz), 3.84 (s, 9H), 3.77 (s, 3H), 3.73 (s, 3H), 2.65–2.50 (b, 1H), 2.47–2.42(m, 2H), 2.29–2.04 (m, 4H), 1.91–1.84 (m, 2H), 1.73 (s, 3H); $^{13}$C NMR δ153.7, 152.9, 150.6, 136.7, 133.6, 133.3, 131.9, 131.2, 130.1, 129.9, 129.2, 127.3, 124.7, 113.1, 112.4, 111.5, 105.8, 102.9, 70.7, 60.9, 56.1, 55.8, 36.2, 35.4, 33.2, 32.8, 28.7, 16.6; MS (EI) m/z (rel. intensity) 482 (M$^+$, 2), 464 (5), 255 (65), 207 (100); HRMS (EI) calculated for $C_{29}H_{38}O_6$: 482.2668, found: 482.2662.

Although the compounds and methods of the present invention have been described in terms of preferred embodiments, it will be apparent to those skilled in the art that variations may be applied to the compositions and/or methods and in the steps or in the sequence of steps of the method described herein without departing from the concept, spirit and scope of the invention. Additionally, those skilled in the art will appreciate that other substituents could be used instead of those outlined herein without departing from the scope of the invention.

More specifically, it will be appreciated that certain agents that are both chemically and physiologically related may be substituted for the agents described herein with comparable results. All such similar substitutes and modifications apparent to those skilled in the art are deemed to be within the spirit, scope and concept of the present invention defined by the appended claims.

What is claimed is:
1. A compound according to the structural formula:

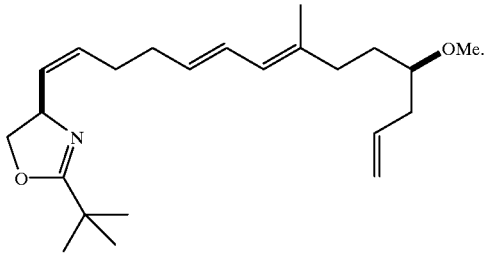

2. A compound according to the formula:

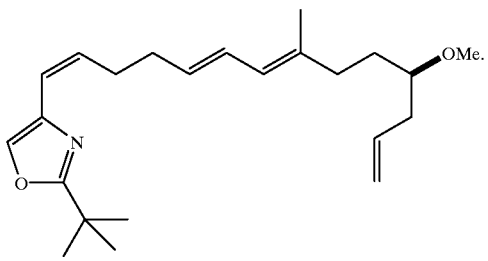

3. A compound according to the structural formula:

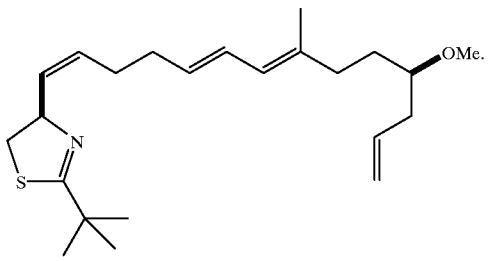

4. A compound according to the structural formula:
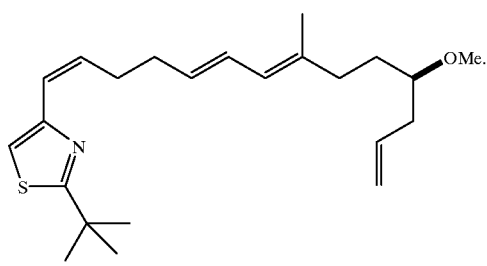
5. A compound according to the structural formula:
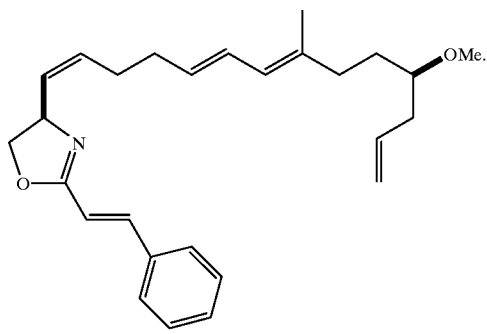
6. A compound according to the structural formula:
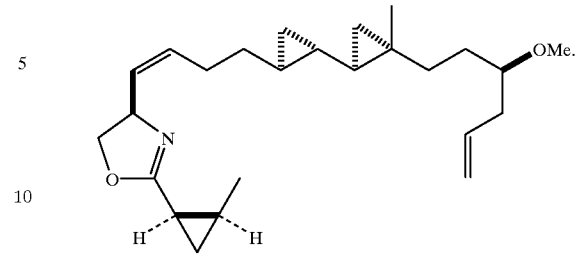
7. A compound according to the structural formula:
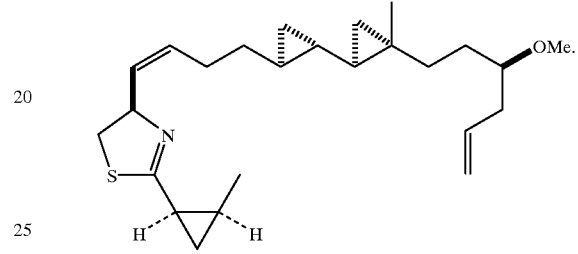
* * * * *